US009389179B2

(12) United States Patent
Sugimoto et al.

(10) Patent No.: US 9,389,179 B2
(45) Date of Patent: Jul. 12, 2016

(54) ANALYSIS APPARATUS AND ELECTRONIC DEVICE

(71) Applicant: Seiko Epson Corporation, Tokyo (JP)

(72) Inventors: Mamoru Sugimoto, Chino (JP); Megumi Enari, Suwa (JP)

(73) Assignee: Seiko Epson Corporation (JP)

( * ) Notice: Subject to any disclaimer, the term of this patent is extended or adjusted under 35 U.S.C. 154(b) by 0 days.

(21) Appl. No.: 14/623,114

(22) Filed: Feb. 16, 2015

(65) Prior Publication Data

US 2015/0233822 A1    Aug. 20, 2015

(30) Foreign Application Priority Data

Feb. 17, 2014 (JP) ................. 2014-027823

(51) Int. Cl.
  *G01J 4/00* (2006.01)
  *G01N 21/552* (2014.01)
  *G01N 21/41* (2006.01)
  *G01N 21/65* (2006.01)
(52) U.S. Cl.
  CPC .............. *G01N 21/553* (2013.01); *G01N 21/41* (2013.01); *G01N 21/658* (2013.01)
(58) Field of Classification Search
  CPC ........................................................ G01J 4/00
  USPC ................................. 356/369, 445
  See application file for complete search history.

(56) References Cited

U.S. PATENT DOCUMENTS

| 3,979,184 | A | 9/1976 | Giaever | |
|---|---|---|---|---|
| 7,351,588 | B2 | 4/2008 | Poponin | |
| 7,399,445 | B2 * | 7/2008 | Kuroda | G01N 21/554 356/300 |
| 7,639,355 | B2 * | 12/2009 | Fattal | B82Y 15/00 356/301 |
| 7,643,156 | B2 | 1/2010 | Naya et al. | |
| 7,705,989 | B2 | 4/2010 | Chaton et al. | |
| 7,733,491 | B2 * | 6/2010 | Kuroda | G01N 21/554 356/445 |
| 7,999,934 | B2 | 8/2011 | Naya et al. | |
| 8,023,114 | B2 | 9/2011 | Yamamichi et al. | |
| 8,314,935 | B2 | 11/2012 | Handa et al. | |

(Continued)

FOREIGN PATENT DOCUMENTS

| EP | 1857810 A1 | 11/2007 |
|---|---|---|
| EP | 2372348 A1 | 10/2011 |

(Continued)

OTHER PUBLICATIONS

Extended European Search Report for Application No. EP 15 15 5031 dated Jul. 13, 2015 (9 pages).

(Continued)

*Primary Examiner* — Roy M Punnoose
(74) *Attorney, Agent, or Firm* — Harness, Dickey & Pierce, P.L.C.

(57) ABSTRACT

An analysis apparatus includes an electric field enhancing element including a metallic layer, a transmissive layer on the metallic layer and transmitting excitation light, and metallic particles on the transmissive layer with first and second pitches in first and second directions; a light source irradiating the element with first direction linearly polarized light, second direction linearly polarized light, and/or circularly polarized light as the excitation light; and a detector detecting light from the element. The pitches are selected relative to the pitch of a diffraction grating. The thickness of the transmissive layer is selected relative to the wavelength of the excitation light.

10 Claims, 20 Drawing Sheets

(56) References Cited

U.S. PATENT DOCUMENTS

| | | | |
|---|---|---|---|
| 8,817,263 B2 | 8/2014 | Sugimoto et al. | |
| 8,836,947 B2 * | 9/2014 | Amako | G01N 21/55 356/445 |
| 9,057,697 B2 * | 6/2015 | Amako | G01N 21/554 |
| 2003/0059855 A1 | 3/2003 | Cunningham et al. | |
| 2006/0194344 A1 | 8/2006 | Saito | |
| 2006/0209413 A1 | 9/2006 | Kim et al. | |
| 2009/0002701 A1 | 1/2009 | Fattal et al. | |
| 2010/0220328 A1 | 9/2010 | Isaka et al. | |
| 2010/0233825 A1 | 9/2010 | Yamada et al. | |
| 2011/0114859 A1 | 5/2011 | Amako et al. | |
| 2011/0164252 A1 | 7/2011 | Handa et al. | |
| 2011/0267613 A1 | 11/2011 | Amako et al. | |
| 2011/0273771 A1 | 11/2011 | Oigawa et al. | |
| 2012/0062881 A1 | 3/2012 | Sakagami et al. | |
| 2012/0062882 A1 | 3/2012 | Sakagami et al. | |
| 2012/0062884 A1 | 3/2012 | Sakagami et al. | |
| 2012/0105853 A1 | 5/2012 | Pang et al. | |
| 2012/0238471 A1 | 9/2012 | Pinchuk | |
| 2012/0274935 A1 | 11/2012 | Yamada et al. | |
| 2012/0276549 A1 | 11/2012 | Cunningham et al. | |
| 2012/0291213 A1 | 11/2012 | Wu et al. | |
| 2012/0309080 A1 | 12/2012 | Cunningham et al. | |
| 2012/0322977 A1 | 12/2012 | Hill | |
| 2012/0327417 A1 | 12/2012 | Amako et al. | |
| 2013/0092823 A1 | 4/2013 | Amako et al. | |
| 2013/0148194 A1 | 6/2013 | Altug et al. | |
| 2013/0176562 A1 | 7/2013 | Shioi et al. | |
| 2013/0182257 A1 | 7/2013 | Sugimoto et al. | |
| 2013/0182258 A1 | 7/2013 | Amako et al. | |
| 2014/0242571 A1 * | 8/2014 | Sugimoto | G01N 21/658 435/5 |
| 2014/0242573 A1 * | 8/2014 | Sugimoto | G01N 21/658 435/5 |
| 2014/0255913 A1 * | 9/2014 | Sugimoto | G01N 21/65 435/5 |
| 2015/0070693 A1 * | 3/2015 | Sugimoto | G01N 21/55 356/301 |
| 2015/0098085 A1 | 4/2015 | Mano | |
| 2015/0138543 A1 | 5/2015 | Sugimoto et al. | |
| 2015/0233822 A1 | 8/2015 | Sugimoto et al. | |
| 2015/0233835 A1 * | 8/2015 | Sugimoto | G01N 21/658 600/310 |

FOREIGN PATENT DOCUMENTS

| | | |
|---|---|---|
| JP | 61-037581 | 8/1986 |
| JP | 2006-003149 A | 1/2006 |
| JP | 2007-024870 A | 2/2007 |
| JP | 2007-064968 A | 3/2007 |
| JP | 2007-508536 A | 4/2007 |
| JP | 2007-538264 A | 12/2007 |
| JP | 2008-014933 A | 1/2008 |
| JP | 2009-085724 A | 4/2009 |
| JP | 2009-115492 A | 5/2009 |
| JP | 2009-115546 A | 5/2009 |
| JP | 2010-531995 A | 9/2010 |
| JP | 2012-132804 A | 7/2012 |
| JP | 2013-148420 A | 8/2013 |
| JP | 2013-148421 A | 8/2013 |
| JP | 2013-221883 A | 10/2013 |
| JP | 2013-231682 A | 11/2013 |
| WO | WO-2005-033335 A2 | 4/2005 |
| WO | WO-2005-114298 A2 | 12/2005 |
| WO | WO-2005-121754 A1 | 12/2005 |
| WO | WO-2009-002524 A2 | 12/2008 |
| WO | WO-2012-011998 A2 | 1/2012 |
| WO | WO-2013-157233 A1 | 10/2013 |
| WO | WO-2013-168401 A1 | 11/2013 |

OTHER PUBLICATIONS

Yizhuo Chu et al., "Double Resonance Surface Enhanced Raman Scattering Substrates: An Intuitive Coupled Oscillator Model", Optics Express, vol. 19, No. 16 (Aug. 1, 2011) (pp. 14919-14928).

Jean Cesario et al. "Electromagnetic Coupling Between a Metal Nanoparticle Grating and a Metallic Surface", Optics Letters, vol. 30, No. 24 (Dec. 15, 2005) (pp. 3404-3406).

Yizhuo Chu et al., "Experimental Study of the Interaction Between Localized and Propagating Surface Plasmons", Optics Letters, vol. 34, No. 3 (Feb. 1, 2009) (pp. 244-246).

Extended European Search Report for Application No. EP 14 15 7592 dated Oct. 2, 2014 (10 pages).

Chu, Y. et al., "Double-resonance plasmon substrates for surface-enhanced Raman scattering with enhancement at excitation and Stokes frequencies", School of Engineering and Applied Sciences, Harvard University, ACS NANO, vol. 4, No. 5, 2010 (pp. 2804-2810).

Extended European Search Report for Application No. EP 14 15 7811 dated Jul. 14, 2014 (8 pages).

Ordal, M.A. et al., "Optical Properties of the Metals Al, Co, Cu, Au, Fe, Pb, Ni, Pd, Pt, Ag, Ti, and W in the Infrared and Far Infrared", Applied Optics, vol. 22, No. 7, Apr. 1, 1983, pp. 1099-1120.

* cited by examiner

FIG. 17A
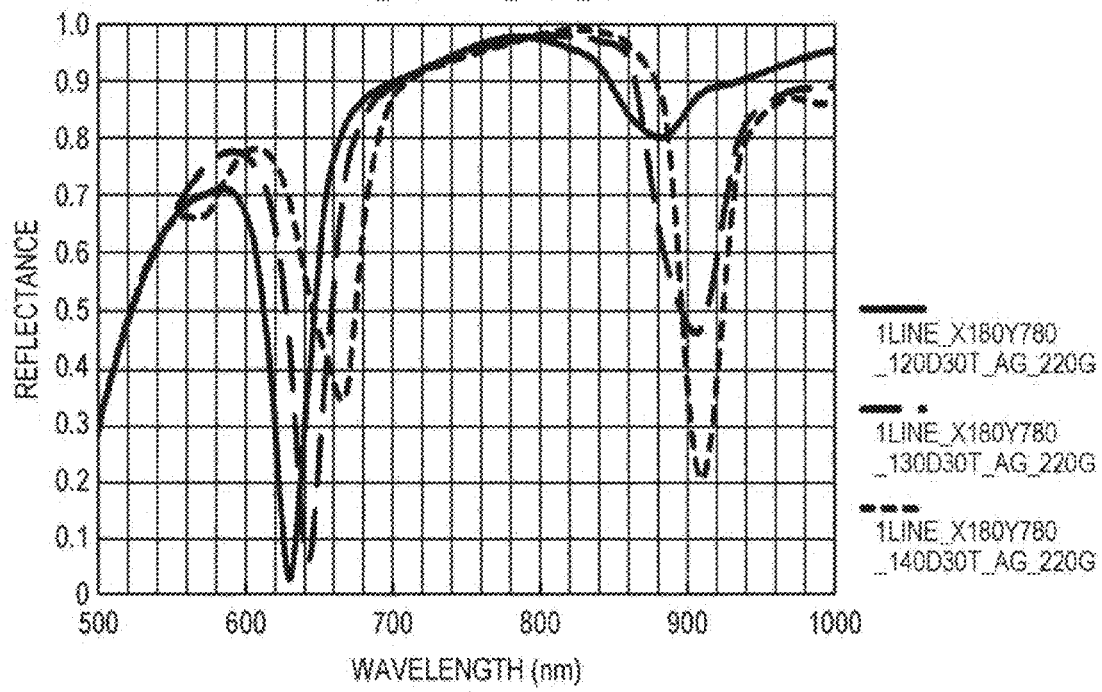
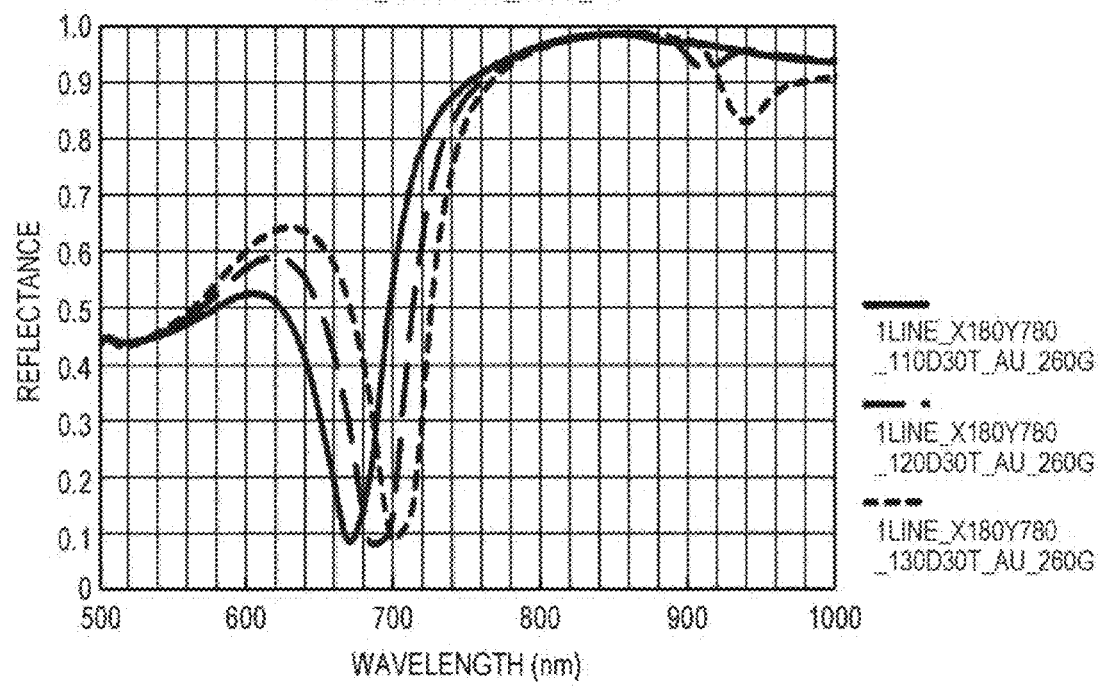
FIG. 17B

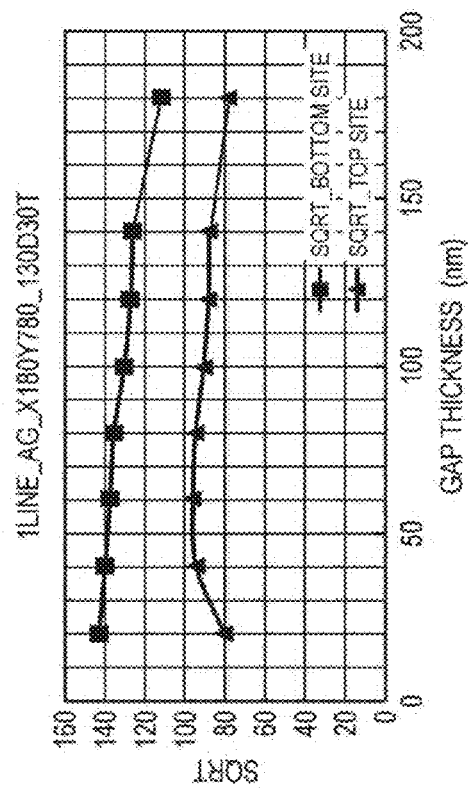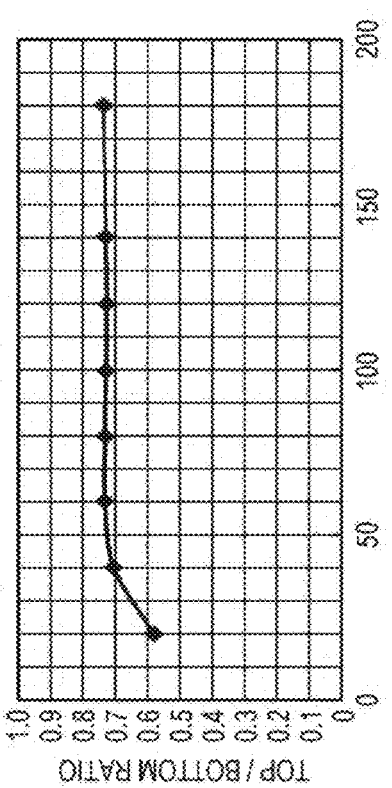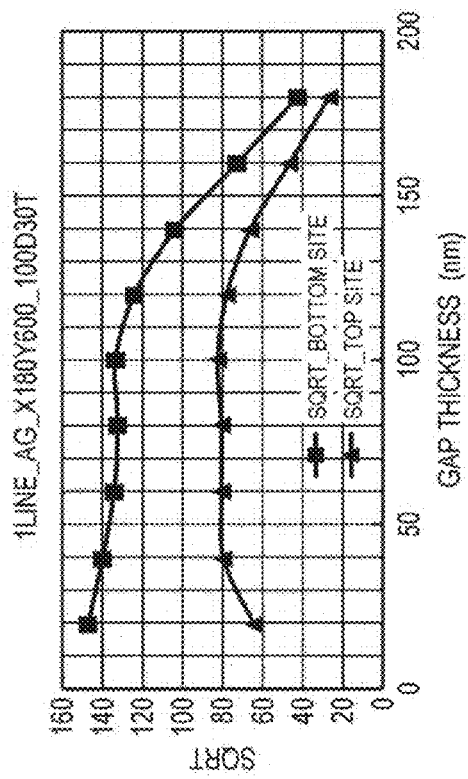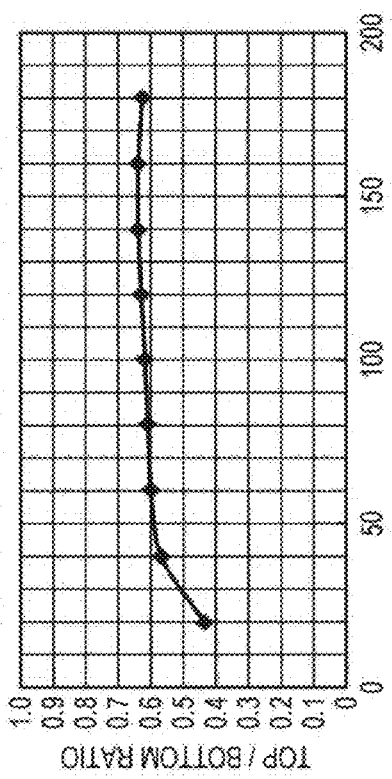
FIG. 19A
FIG. 19B
FIG. 19C
FIG. 19D

FIG. 24A
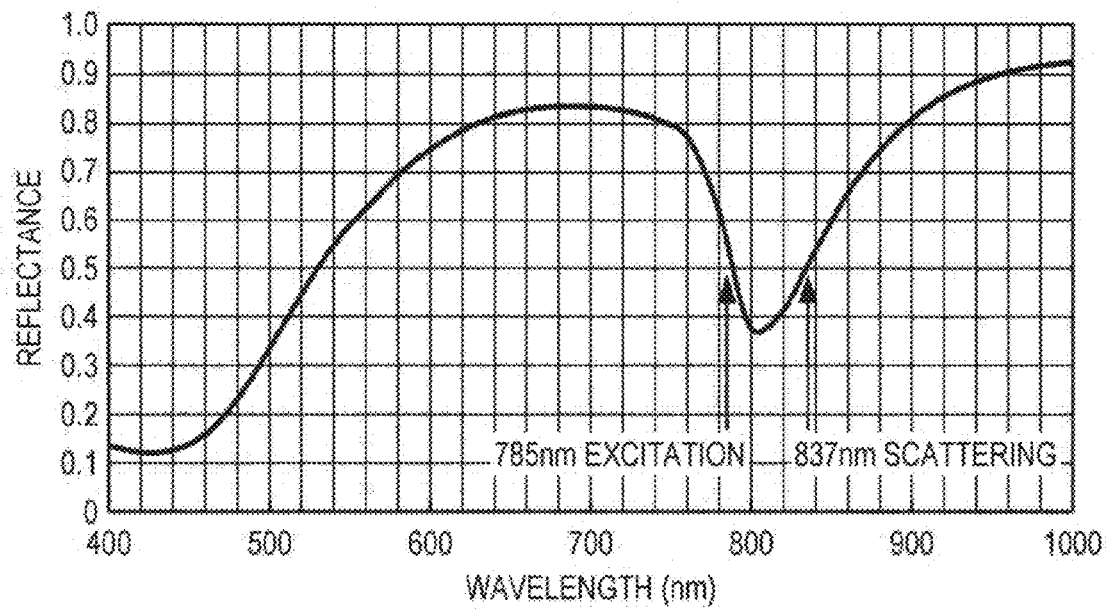
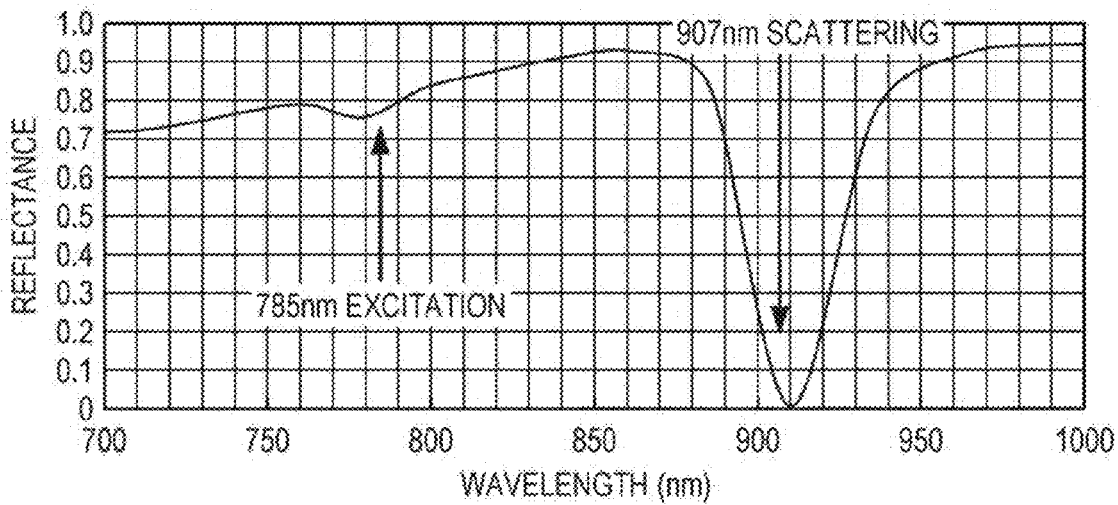
FIG. 24B

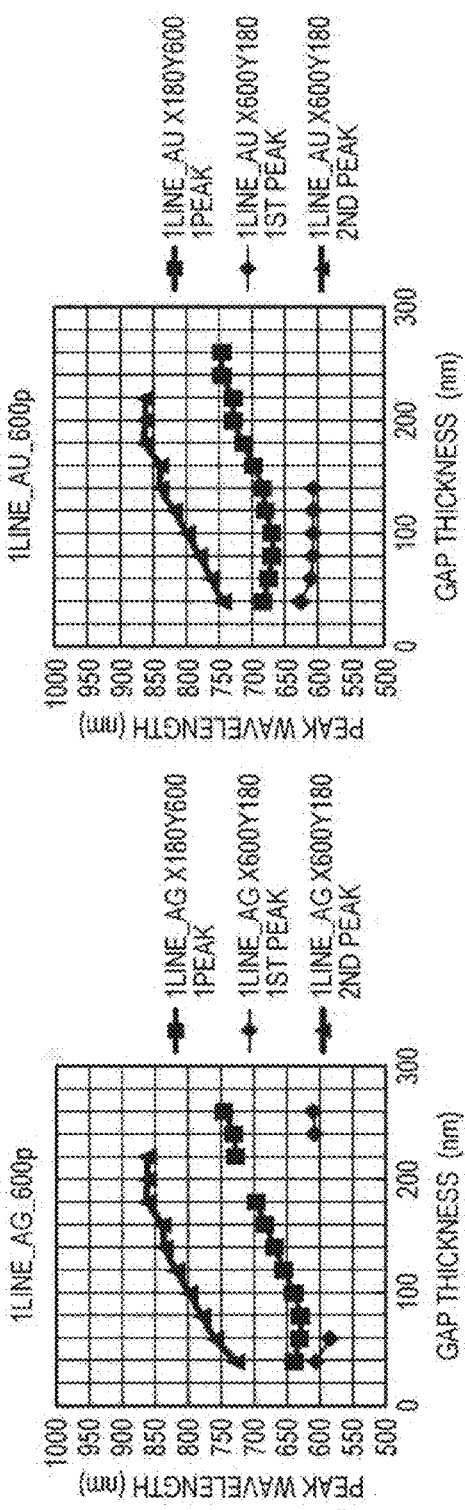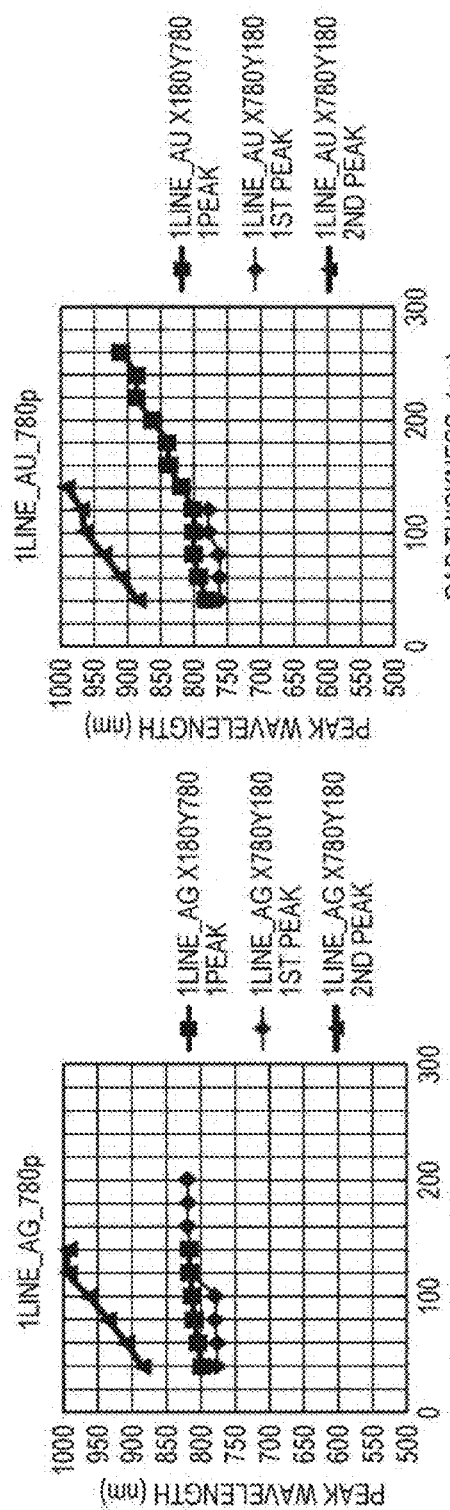

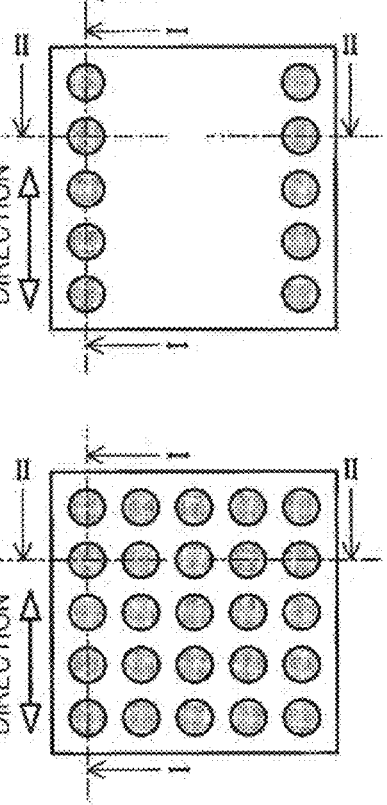

ANALYSIS APPARATUS AND ELECTRONIC DEVICE

BACKGROUND

1. Technical Field

The present invention relates to an analysis apparatus and an electronic device.

2. Related Art

Recently, a demand for medical diagnosis, food inspection, or the like has increased greatly, and there has been a need to develop compact and high-speed sensing techniques. Various sensors commencing with an electrochemical method have been considered, and an interest with respect to a sensor using a surface plasmon resonance (SPR) has increased because integration is possible, the cost is reduced, and any measurement environment may be used. For example, a technology which detects a presence or absence of adsorption of a substance such as a presence or absence of adsorption of an antigen in an antigen-antibody reaction by using surface plasmon generated in a metallic thin film disposed on a total reflection prism surface has been known.

In addition, a method is also considered in which Raman scattering of a substance attached to a sensor portion is detected by using surface enhanced Raman scattering (SERS), and the attached substance is determined. SERS is a phenomenon in which Raman scattering light is enhanced $10^2$ to $10^{14}$ times in a surface of metal in a nanometer scale. When a target substance which is in a state of being adsorbed onto the surface is irradiated with excitation light such as laser, light (Raman scattering light) having a wavelength which is slightly shifted from a wavelength of the excitation light by vibration energy of the substance (molecules) is scattered. When the scattering light is subjected to spectroscopic processing, a spectrum (a fingerprint spectrum) inherent to a type of substance (molecular species) is obtained. By analyzing a position or a shape of the fingerprint spectrum, it is possible to determine the substance with extremely high sensitivity.

It is preferable that such a sensor has a great enhancement degree of light on the basis of surface plasmon excited by light irradiation.

For example, in JP-T-2007-538264, a mutual interaction between localized surface plasmon (LSP) and surface plasmon polariton (SPP) is disclosed, and some parameters of a gap type surface plasmon polariton (GSPP) model are disclosed.

The GSPP of JP-T-2007-538264 has a dimension in which a size of particles causing a plasmon resonance is 50 nm to 200 nm, a periodic interparticle interval is shorter than an excitation wavelength, and a thickness of a dielectric body separating a particle layer from a mirror layer is 2 nm to 40 nm, and is in a regular array of plasmon resonance particles which are densely filled by an interparticle interval obtained by adding 0 nm to 20 nm to a particle dimension.

However, in a sensor having a structure disclosed in JP-T-2007-538264, the thickness of the dielectric body separating the particle layer from the mirror layer is 2 nm to 40 nm, and according to a consideration of the inventors, it is found that a peak of an electric field enhancement degree in wavelength dependent properties (an enhancement degree spectrum or a reflectance spectrum) is broad, but an enhancement degree which is totally low and insufficient is obtained. In addition, in the sensor disclosed in JP-T-2007-538264, it is found that when a dimension of a plurality of particles is uneven (when a variation occurs), a wavelength having a peak in the enhancement degree spectrum is greatly shifted.

SUMMARY

An advantage of some aspects of the invention is to provide an analysis apparatus and an electronic device in which a high enhancement degree is obtained in an enhancement degree spectrum, and a target substance is able to be detected and analyzed with high sensitivity. Another advantage of some aspects of the invention is to provide an analysis apparatus and an electronic device in which the target substance is easily attached to a position having a high enhancement degree. Still another advantage of some aspects of the invention is to provide an analysis apparatus and an electronic device in which an allowable range of a variation in manufacturing is wide.

The invention can be implemented as the following aspects or application examples.

An aspect of the invention is directed to an analysis apparatus including an electric field enhancing element including a metallic layer, a light-transmissive layer which is disposed on the metallic layer and transmits excitation light, and a plurality of metallic particles which is disposed on the light-transmissive layer, and is arranged in a first direction at a first pitch and arranged in a second direction intersecting with the first direction at a second pitch; a light source irradiating the electric field enhancing element with at least one of linearly polarized light which is polarized in the first direction, linearly polarized light which is polarized in the second direction, and circularly polarized light as the excitation light; and a detector detecting light emitted from the electric field enhancing element, in which arrangement of the metallic particles of the electric field enhancing element satisfies a relationship of the following expression (1):

$$P1 < P2 \leq Q + P1 \quad (1)$$

in which P1 is the first pitch, P2 is the second pitch, and Q is a pitch of a diffraction grating satisfying the following expression (2) when an angular frequency of localized plasmon excited to a row of the metallic particles is ω, a dielectric constant of metal configuring the metallic layer is $\in(\omega)$, a dielectric constant in the vicinity of the metallic particles is ∈, a speed of light in vacuum is c, and an inclined angle from a thickness direction of the metallic layer which is an irradiation angle of the excitation light is θ:

$$(\omega/c) \cdot \{\in \cdot \in(\omega)/(\in + \in(\omega))\}^{1/2} = \in^{1/2} \cdot (\omega/c) \cdot \sin\theta + 2a\pi/Q$$
$$(a = \pm 1, \pm 2, \dots) \quad (2), \text{ and}$$

when a thickness of the light-transmissive layer is G nm, an effective refractive index of the light-transmissive layer is $n_{eff}$, and a wavelength of the excitation light is $\lambda_i$ nm, a relationship of the following expression (3) is satisfied:

$$20 \text{ nm} < G \cdot (n_{eff}/1.46) \geq 160 \text{ nm} \cdot (\lambda_i/785 \text{ nm}) \quad (3)$$

According to the analysis apparatus, an extremely high enhancement degree is obtained in an enhancement degree spectrum, and a target substance is able to be detected and analyzed with high sensitivity. In addition, a position in which a high enhancement degree of the analysis apparatus is obtained exists on at least an upper surface side of metallic particles, and thus the target substance is easily in contact with the position, and it is possible to detect and analyze the target substance with high sensitivity.

In the analysis apparatus according to the aspect of the invention, the G, the $n_{eff}$, and the X may satisfy a relationship of the following expression (4).

$$30 \text{ nm} \geq G \cdot (n_{eff}/1.46) \geq 160 \text{ nm} \cdot (\lambda_i/785 \text{ nm}) \quad (4)$$

According to the analysis apparatus with this configuration, the relationship of 30 nm≥G·($n_{eff}$/1.46) is satisfied, and thus it is possible to increase an allowable range of a variation in manufacturing.

Another aspect of the invention is directed to an analysis apparatus including an electric field enhancing element including a metallic layer, a light-transmissive layer which is disposed on the metallic layer and transmits excitation light, and a plurality of metallic particles which is disposed on the light-transmissive layer, and is arranged in a first direction at a first pitch and arranged in a second direction intersecting with the first direction at a second pitch; a light source irradiating the electric field enhancing element with at least one of linearly polarized light which is polarized in the first direction, linearly polarized light which is polarized in the second direction, and circularly polarized light as the excitation light; and a detector detecting light emitted from the electric field enhancing element, in which arrangement of the metallic particles of the electric field enhancing element satisfies a relationship of the following expression (1):

$$P1 < P2 \geq Q + P1 \tag{1}$$

in which P1 is the first pitch, P2 is the second pitch, and Q is a pitch of a diffraction grating satisfying the following expression (2) when an angular frequency of localized plasmon excited to a row of the metallic particles is $\omega$, a dielectric constant of metal configuring the metallic layer is $\in(\omega)$, a dielectric constant in the vicinity of the metallic particles is $\in$, a speed of light in vacuum is c, and an inclined angle from a thickness direction of the metallic layer which is an irradiation angle of the excitation light is $\theta$:

$$(\omega/c) \cdot \{\in \cdot \in(\omega)/(\in + \in(\omega))\}^{1/2} = \in^{1/2} \cdot (\omega/c) \cdot \sin\theta + 2a\pi/Q$$
$$(a = \pm 1, \pm 2, \ldots) \tag{2},$$

the light-transmissive layer is formed of a laminated body in which m layers are laminated, m is a natural number, the light-transmissive layer is formed by laminating a first light-transmissive layer, a second light-transmissive layer, ..., a (m−1)-th light-transmissive layer, and a m-th light-transmissive layer in this order from the metallic particle side to the metallic layer side, and when a refractive index in the vicinity of the metallic particles is $n_0$, an angle between a normal direction of the metallic layer and an incident direction of the excitation light is $\theta_0$, an angle between the normal direction of the metallic layer and an incident direction of refracting light of the excitation light in the m-th light-transmissive layer with respect to the metallic layer is $\theta_m$, a refractive index of the m-th light-transmissive layer is $n_m$, a thickness of the m-th light-transmissive layer is $G_m$ nm, and a wavelength of the excitation light is $\lambda_i$ nm, relationships of the following expression (5) and expression (6) are satisfied.

$$n_0 \cdot \sin\theta_0 = n_m \cdot \sin\theta_m \tag{5}$$

$$20[\text{nm}] < \sum_{m=1}^{m} \{(G_m \cdot \cos\theta_m) \cdot (n_m/1.46)\} \leq 160[\text{nm}] \cdot \lambda_i / 785[\text{nm}] \tag{6}$$

According to the analysis apparatus, an extremely high enhancement degree is obtained in an enhancement degree spectrum, and a target substance is able to be detected and analyzed with high sensitivity. In addition, a position in which a high enhancement degree of the analysis apparatus is obtained exists on at least an upper surface side of metallic particles, and thus the target substance is easily in contact with the position, and it is possible to detect and analyze the target substance with high sensitivity.

In the analysis apparatus according to the aspect of the invention, the $\theta_m$, the $n_m$, the $G_m$, and the $\lambda_i$ may satisfy a relationship of the following expression (7).

$$30[\text{nm}] \leq \sum_{m=1}^{m} \{(G_m \cdot \cos\theta_m) \cdot (n_m/1.46)\} \leq 160[\text{nm}] \cdot \lambda_i / 785[\text{nm}] \tag{7}$$

According to the analysis apparatus with this configuration, the relationship of:

$$30[\text{nm}] \leq \sum_{m=1}^{m} \{(G_m \cdot \cos\theta_m) \cdot (n_m/1.46)\}$$

is satisfied, and thus it is possible to increase an allowable range of a variation in manufacturing.

In the analysis apparatus according to the aspect of the invention, a ratio of intensity of localized surface plasmon excited to a corner portion of the metallic particles on a side away from the light-transmissive layer to intensity of localized surface plasmon excited to a corner portion of the metallic particles on a side close to the light-transmissive layer may be constant regardless of the thickness of the light-transmissive layer.

According to the analysis apparatus with this configuration, even when the thickness of the light-transmissive layer varies, the ratio of the intensity of the localized surface plasmon excited to an upper surface side of the metallic particles to the intensity of the localized surface plasmon excited to a lower surface side of the metallic particles does not vary, and thus the analysis apparatus is more easily manufactured.

Still another aspect of the invention is directed to an electronic device including the analysis apparatus described above; a calculation unit which calculates medical health information on the basis of detection information from the detector; a storage unit which stores the medical health information; and a display unit which displays the medical health information.

According to the electronic device, an enhancement degree is extremely high, and a target substance is able to be detected and analyzed with high sensitivity, and thus medical health information with high sensitivity and high accuracy is able to be provided.

BRIEF DESCRIPTION OF THE DRAWINGS

Embodiments of the invention will be described with reference to the accompanying drawings, wherein like numbers reference like elements.

FIGS. 17A and B are reflectance spectrums of the model according to the experimental example.

FIGS. 19A-D are graphs illustrating the light-transmissive layer thickness dependent properties of SQRT and the top/bottom ratio of the model according to the experimental example.

FIGS. 24A and B are reflectance spectrums of the model according to the experimental example.

FIGS. 25A-D are graphs illustrating the light-transmissive layer thickness dependent properties of the minimum wavelength having a peak in the reflectance spectrum of the model according to the experimental example.

FIGS. 27A-D are schematic views illustrating a relationship between arrangement of the metallic particles and LSP and PSP.

DESCRIPTION OF EXEMPLARY EMBODIMENTS

Hereinafter, some embodiments of the invention will be described. The following embodiments describe examples of the invention. The invention is not limited to the following embodiments, and includes various modifications performed within a range not changing the gist of the invention. Furthermore, all of the following configurations are not essential configurations of the invention.

1. Electric Field Enhancing Element

Figure 1:
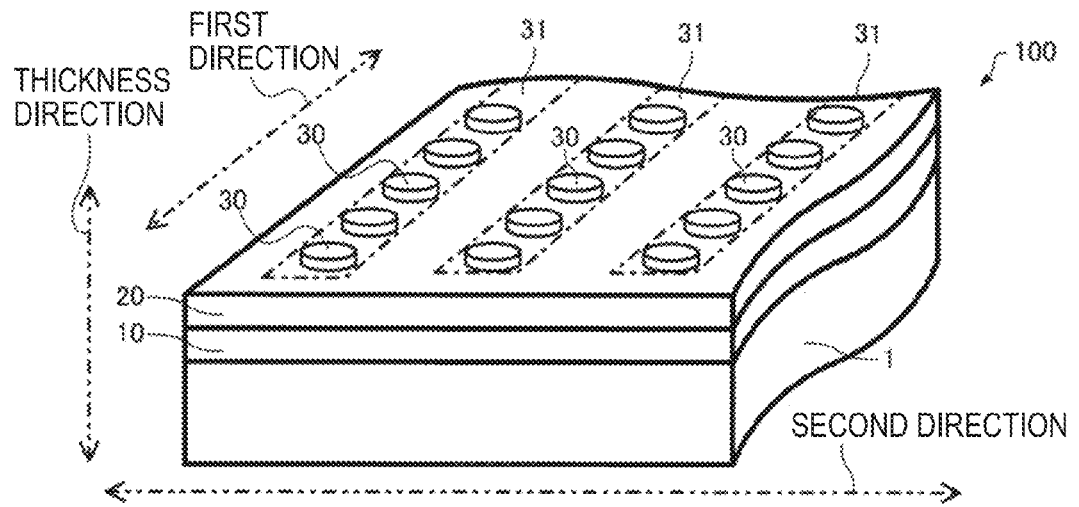
FIG. 1 is a perspective view schematically illustrating a main part of an electric field enhancing element according to an embodiment.
Figure 2:
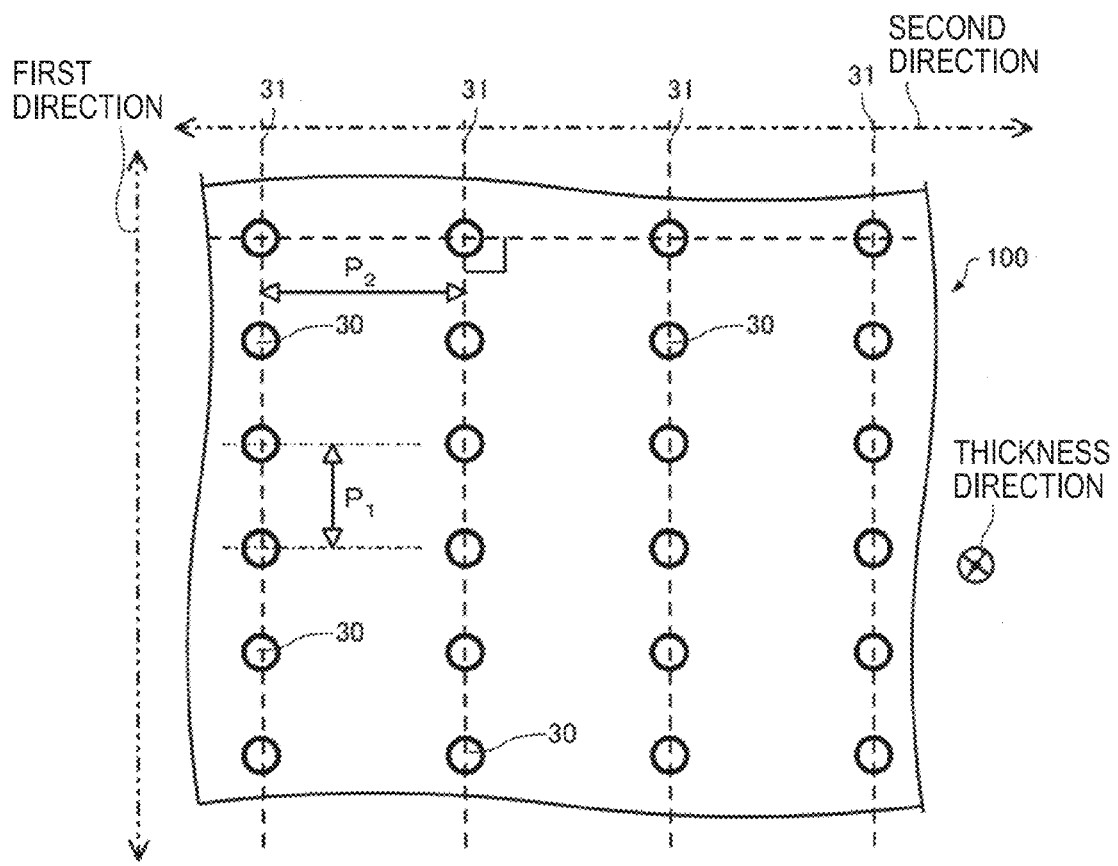
FIG. 2 is a schematic view of the main part of the electric field enhancing element according to the embodiment seen in a plan view.
Figure 3:
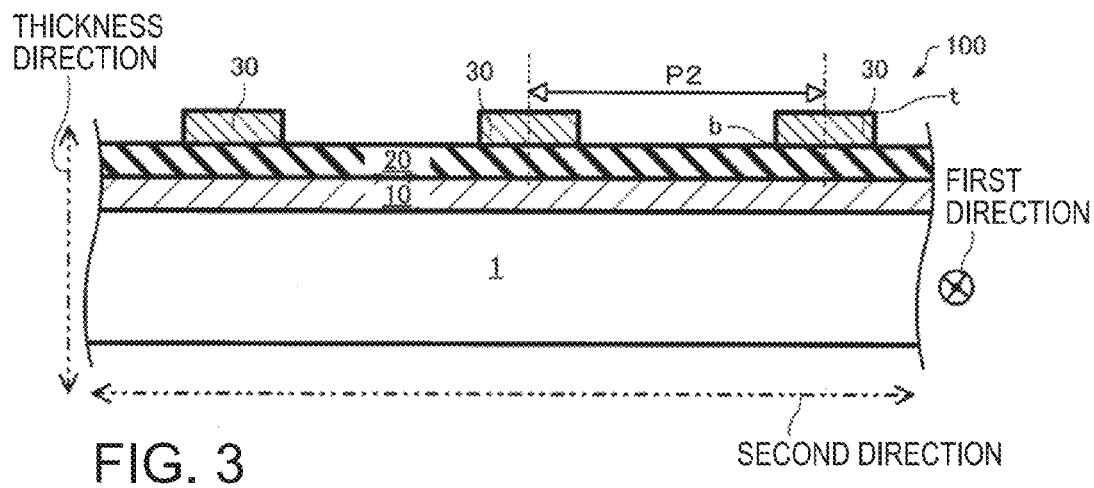
FIG. 3 is a schematic view of a cross-sectional surface of the main part of the electric field enhancing element according to the embodiment.
Figure 4:
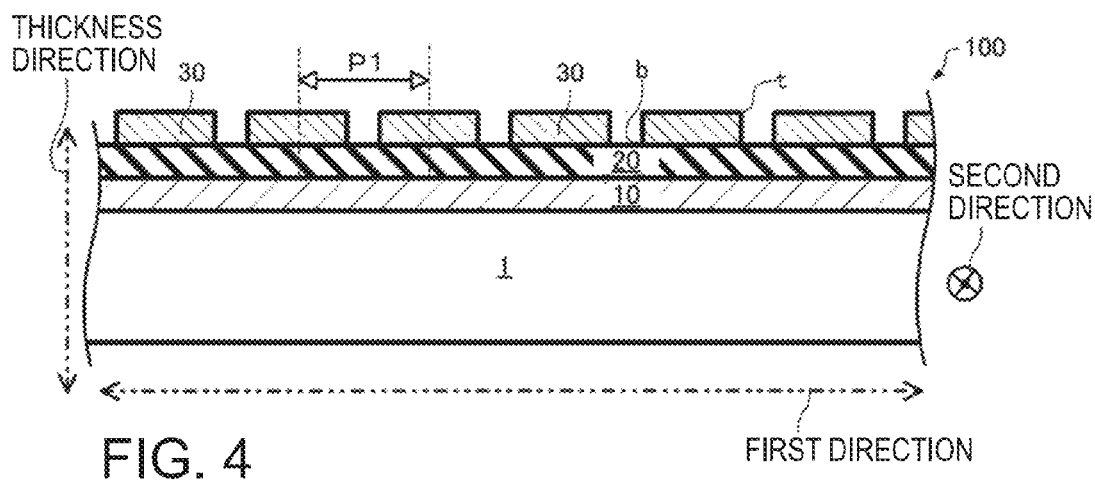
FIG. 4 is a schematic view of the cross-sectional surface of the main part of the electric field enhancing element according to the embodiment.

FIG. 1 is a perspective view of an electric field enhancing element 100 according to an example of an embodiment. FIG. 2 is a schematic view of the electric field enhancing element 100 according to an example of the embodiment seen in a plan view (seen from a thickness direction of a light-transmissive layer). FIG. 3 and FIG. 4 are schematic views of a cross-sectional surface of the electric field enhancing element 100 according to an example of the embodiment. The electric field enhancing element 100 of this embodiment includes a metallic layer 10, a light-transmissive layer 20, and metallic particles 30.

1.1. Metallic Layer

The metallic layer 10 is not particularly limited insofar as a surface of metal is provided, and for example, may be in the shape of a thick plate, a film, a layer, or a membrane. The metallic layer 10, for example, may be disposed on a substrate 1. In this case, the substrate 1 is not particularly limited, and as the substrate 1, a substrate which does not have an influence on propagating surface plasmon excited to the metallic layer 10 is preferable. As the substrate 1, for example, a glass substrate, a silicon substrate, a resin substrate, and the like are included. A shape of a surface of the substrate 1 on which the metallic layer 10 is disposed is not particularly limited. When a regular structure is formed on a surface of the metallic layer 10, the surface may correspond to the regular structure, and when the surface of the metallic layer 10 is a flat surface, the surface of the substrate 1 may be a flat surface. In examples of FIG. 1 to FIG. 4, the metallic layer 10 is disposed on the surface (a flat surface) of the substrate 1.

Here, an expression of the flat surface does not indicate a mathematically strict flat surface which is flat (smooth) without having a few concavities and convexities. For example, when there are concavities and convexities due to a constituent atom, concavities and convexities due to a secondary structure (crystal, grain aggregation, a grain boundary, and the like) of a constituent substance, or the like in the surface, the surface may not be strictly a flat surface from a microscopic viewpoint. However, even in this case, from a macroscopic viewpoint, the concavities and convexities are not remarkable, and are observed to the extent of not having difficulty in referring to the surface as a flat surface. Therefore, herein, insofar as a flat surface is able to be recognized from such a macroscopic viewpoint, a surface is referred to as a flat surface.

In addition, in this embodiment, a thickness direction of the metallic layer 10 is identical to a thickness direction of the light-transmissive layer 20 described later. Herein, when the thickness direction of the metallic layer 10 or the thickness direction of the light-transmissive layer 20 is described with respect to the metallic particles 30, or the like, the thickness direction may be referred to as a thickness direction, a height direction, and the like. In addition, for example, when the metallic layer 10 is disposed on the surface of the substrate 1, a normal direction of the surface of the substrate 1 may be referred to as a thickness direction, a thickness direction or a height direction.

Further, when seen from the substrate 1, a direction on the metallic layer 10 side may be expressed as a top or an upper side, and a reverse direction may be expressed as a bottom or a lower side. The expression of the upper side and the lower side indicates a direction which is used without any relation to a direction on which gravity acts, and is expressed by suitably determining a direction of a viewpoint or a sight line when viewing an element. In addition, herein, for example, an expression that "a member B is disposed on a member A" indicates a case where the member B is disposed on the member A to be in contact with each other, or a case where the member B is arranged on the member A through other members or a space.

The metallic layer 10, for example, is able to be formed by a method such as vapor deposition, sputtering, casting, and machining. When the metallic layer 10 is disposed on the substrate 1, the metallic layer 10 may be disposed on the entire surface of the substrate 1, or may be disposed on a part of the surface of the substrate 1. A thickness of the metallic layer 10 is not particularly limited insofar as propagating surface plasmon is able to be excited to the surface of the metallic layer 10, or the vicinity of a surface boundary between the metallic layer 10 and the light-transmissive layer 20, and for example, is able to be greater than or equal to 10 nm and less than or equal to 1 mm, preferably greater than or equal to 20 nm and less than or equal to 100 μm, and more preferably greater than or equal to 30 nm and less than or equal to 1 μm.

The metallic layer 10 is formed of metal having an electric field applied by excitation light, and an electric field in which polarization induced by the electric field is vibrated in an antiphase, that is, metal capable of having a dielectric constant in which a real part of a dielectric function is a negative value (a negative dielectric constant), and a dielectric constant of an imaginary part is smaller than an absolute value of a dielectric constant of the real part when a specific electric field is applied. As an example of metal capable of having such a dielectric constant, gold, silver, aluminum, copper, platinum, an alloy thereof, and the like are able to be included. When light in a visible light region is used as the excitation light, it is preferable that the metallic layer 10 includes a layer formed of gold, silver, or copper among the metals. In addition, the surface of the metallic layer 10 (an end surface in the thickness direction) may not be a specific crystal plane. In addition, the metallic layer 10 may be formed of a plurality of metallic layers.

The metallic layer 10 has a function of generating the propagating surface plasmon in the electric field enhancing element 100 of this embodiment. Light is incident on the metallic layer 10 under a condition described later, and thus the propagating surface plasmon is generated in the vicinity of the surface of the metallic layer 10 (an upper end surface of the thickness direction). In addition, herein, quantum of vibration of an electric charge in the vicinity of the surface of the metallic layer 10 and vibration to which an electromagnetic wave is bonded is referred to as surface plasmon polariton (SPP). The propagating surface plasmon generated in the metallic layer 10 is able to mutually interact (hybrid) with localized surface plasmon generated in the metallic particles 30 described later in a constant condition. Further, the metallic layer 10 has a function of a mirror reflecting light (for example, refracting light of the excitation light) toward the light-transmissive layer 20 side.

1.2. Light-Transmissive Layer

The electric field enhancing element 100 of this embodiment includes the light-transmissive layer 20 for separating the metallic layer 10 from the metallic particles 30. In FIG. 1, FIG. 3, and FIG. 4, the light-transmissive layer 20 is illustrated. The light-transmissive layer 20 is able to be in the shape of a film, a layer, or a membrane. The light-transmissive layer 20 is disposed on the metallic layer 10. Accordingly, it is possible to spatially and electrically separate the metallic layer 10 from the metallic particles 30. In addition, the light-transmissive layer 20 is able to transmit the excitation light.

The light-transmissive layer 20, for example, is able to be formed by a method such as vapor deposition, sputtering, CVD, and various coatings. In addition, in a plan view, the light-transmissive layer 20 may be disposed on the entire surface of the metallic layer 10, or may be disposed on a part of the surface of the metallic layer 10.

The light-transmissive layer 20 may have a positive dielectric constant, and for example, is able to be formed of silicon oxide ($SiO_x$, for example, $SiO_2$), aluminum oxide ($Al_xO_y$, for example, $Al_2O_3$), tantalum oxide ($Ta_2O_5$), silicon nitride ($Si_3N_4$), titanium oxide ($TiO_x$, for example, $TiO_2$), high molecules such as a Polymethylmethacrylate (PMMA), Indium. Tin Oxide (ITO), and the like. In addition, the light-transmissive layer 20 is able to be formed of a dielectric body. Further, the light-transmissive layer 20 may be configured of a plurality of layers having materials which are different from each other.

A thickness G of the light-transmissive layer 20 is set such that the propagating surface plasmon of the metallic layer 10 is able to mutually interact with the localized surface plasmon of the metallic particles 30. For example, the thickness G nm of the light-transmissive layer 20 is set as follows.

(i) When an effective refractive index of the light-transmissive layer 20 is $n_{eff}$, and a wavelength of the excitation light is $\lambda_i$ nm, the thickness G nm of the light-transmissive layer 20 is set to satisfy a relationship of the following expression (4).

$$20\text{ nm} < G \cdot (n_{eff}/1.46) \geq 160\text{ nm} \neq (\lambda_i/785\text{ nm}) \quad (4)$$

Here, when the light-transmissive layer 20 is formed of a single layer, the effective refractive index $n_{eff}$ of the light-transmissive layer 20 is identical to a value of a refractive index of a material configuring the single layer. In contrast, when the light-transmissive layer 20 is formed of a plurality of layers, the effective refractive index $n_{eff}$ of the light-transmissive layer 20 is identical to a value (an average value) obtained by dividing a product of a thickness of each layer configuring the light-transmissive layer 20 and a refractive index of each layer by the entire thickness G of the light-transmissive layer 20.

Figure 5:
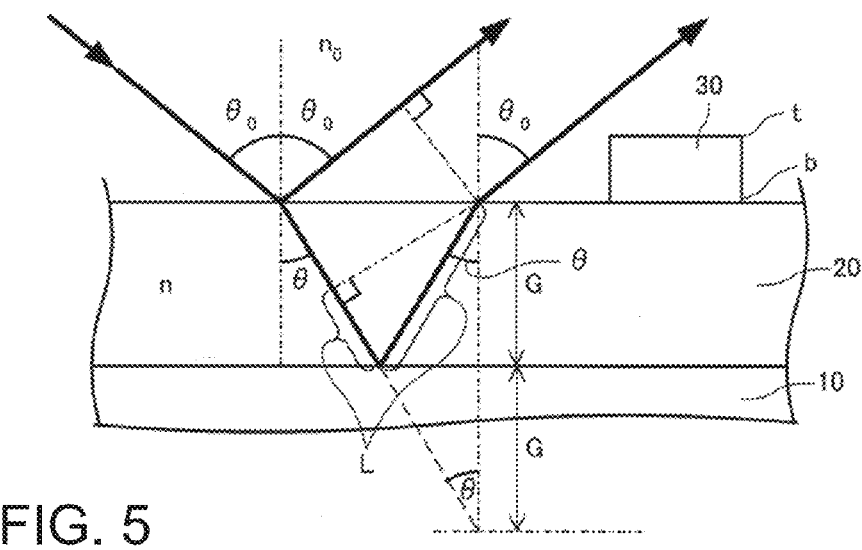
FIG. 5 is a schematic view illustrating an example of a light path of excitation light.

FIG. 5 is a diagram schematically illustrating a light path of the excitation light when the light-transmissive layer 20 is configured of a single layer having a refractive index n. With reference to FIG. 5, in a case where the light-transmissive layer 20 is configured of the single layer having a refractive index n, when the excitation light inclines at an inclined angle $\theta_0$ with respect to a normal direction (the thickness direction) of the light-transmissive layer 20 from a phase having a refractive index of $n_0$, and is incident on the light-transmissive layer 20, the refracting light of the excitation light satisfying a relationship of $n_0 \cdot \sin \theta_0 = n \cdot \sin \theta$ from Snell's law is generated in the light-transmissive layer 20 at the inclined angle $\theta$ with respect to the normal direction of the light-transmissive layer 20 (in the expression, "·" indicates a product).

Then, a light path difference between light reflected by an upper surface of the light-transmissive layer and light reflected by a lower surface of the light-transmissive layer 20 is $2 \cdot n \cdot G \cdot \cos \theta$ (refer to FIG. 5). In addition, a half-wavelength is shifted due to the reflection by the metallic layer 10, and thus when the wavelength of the excitation light is $\lambda_i$, the light path difference is $k \cdot \lambda_i$ (here, k is an integer). Accordingly, $2 \cdot n \cdot G \cdot \cos \theta = k \cdot \lambda_i$ is completed, and a relationship of $\sin \theta = (n_0/n) \cdot \sin \theta_0$ and $\theta = \sin^{-1}\{(n_0/n)\sin \theta_0\}$ is completed.

Figure 6:
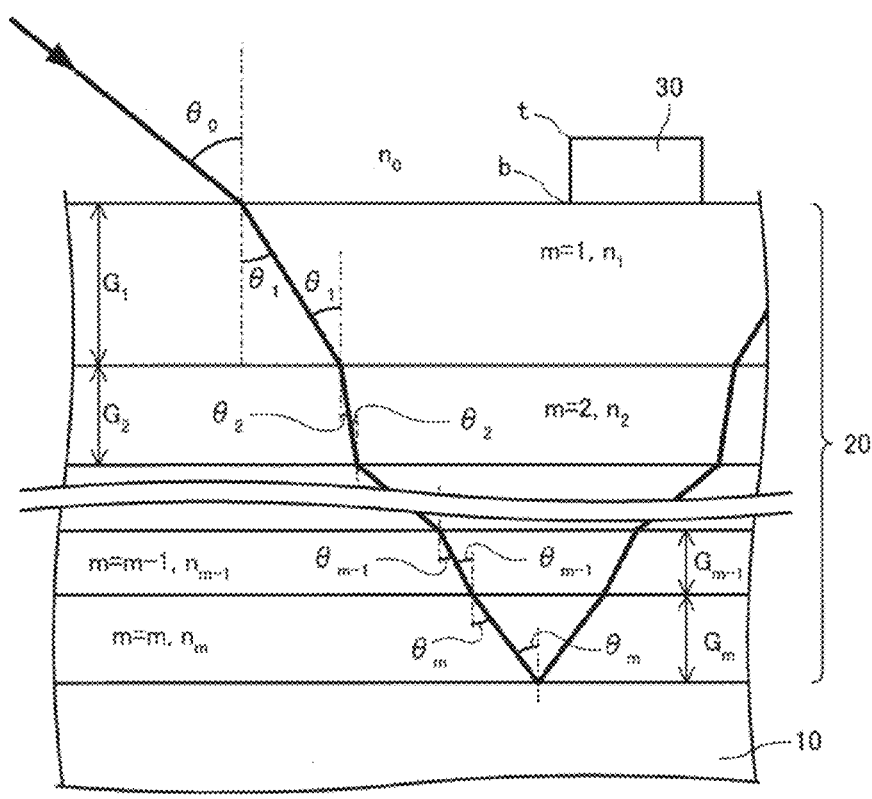
FIG. 6 is a schematic view illustrating an example of the light path of the excitation light.

(ii) FIG. 6 is a diagram schematically illustrating the light path of the excitation light when the light-transmissive layer 20 is configured of a plurality of layers. With reference to FIG. 6, in a case where the light-transmissive layer 20 is configured of the plurality of layers, when the excitation light inclines at the inclined angle $\theta_0$ with respect to the normal direction (the thickness direction) of the light-transmissive layer 20, and is incident on the light-transmissive layer 20, the light-transmissive layer 20 is considered as a light-transmissive layer in which a first light-transmissive layer, a second light-transmissive layer, a (m−1)-th light-transmissive layer, and a m-th light-transmissive layer are laminated in this order from a side away from the metallic layer 10 toward the metallic layer 10 (here, m is an integer greater than or equal to 2). Then, the excitation light inclines at the inclined angle $\theta_0$ with respect to the normal direction (the thickness direction) of the light-transmissive layer 20 from the phase having a refractive index of $n_0$, and is incident on the light-transmissive layer 20. In this case, when an angle between the normal direction of the light-transmissive layer 20 and the refracting light of the excitation light in the m-th light-transmissive layer is $\theta_m$, a refractive index of the m-th light-transmissive layer is $n_m$, and a thickness of the m-th light-transmissive layer is $G_m$ nm, the refracting light of the excitation light satisfying a relationship of $n_0 \cdot \sin \theta_0 = n_m \cdot \sin \theta_m$ from Snell's law is generated in the m-th light-transmissive layer at the inclined angle $\theta_m$ with respect to the normal direction of the light-transmissive layer 20. Accordingly, when the thickness of the m-th light-transmissive layer is $G_m$, and the refractive index of the m-th light-transmissive layer is $n_m$, a light path difference of $2 \cdot n_m \cdot G_m \cdot \cos \theta_m$ is generated in each layer.

According to this, a total light path difference L is $L = \Sigma (2 \cdot n_m \cdot G_m \cdot \cos \theta_m)$. Then, when the light path difference L is an integer times ($k \cdot \lambda_i$) a wavelength of incident light, the light is intensified. In addition, it is understood that in a case of a vertical incidence (an incident direction of the excitation light is parallel with the thickness direction of the light-transmissive layer 20), $\theta_0$ is 0, and a value of $\cos \theta_m$ is 1, and in a case of an oblique incidence, a value of $\cos \theta_m$ is smaller than 1, and thus a thickness $G_m$ in which light is intensified is greater (thicker) in the oblique incidence than in the vertical incidence.

In addition, when the light-transmissive layer 20 is formed of a laminated body in which m layers are laminated (m is a natural number), the thickness G of the light-transmissive layer 20 is considered as the light-transmissive layer 20 in which the first light-transmissive layer, the second light-transmissive layer, the (m−1)-th light transmissive layer, and the m-th light-transmissive layer are laminated from the side away from the metallic layer 10 toward the metallic layer 10. Then, the excitation light inclines at the inclined angle $\theta_0$ with respect to the normal direction (the thickness direction) of the light-transmissive layer 20 from the phase having a refractive index of $n_0$, and is incident on the light-transmissive layer 20. In this case, the angle between the normal direction of the light-transmissive layer 20 and the refracting light of the excitation light in the m-th light-transmissive layer is $\theta_m$, the refractive index of the m-th light-transmissive layer is $n_m$, and the thickness of the m-th light-transmissive layer is $G_m$ nm, the refracting light of the excitation light satisfying a relationship of $n_0 \cdot \sin \theta_0 = n_m \cdot \sin \theta_m$ from Snell's law is generated in the m-th light-transmissive layer at the inclined angle $\theta_m$ with respect to the normal direction of the light-transmissive layer 20.

Then, when the wavelength of the excitation light is $\lambda_i$ nm, relationships of the following expressions (5) and (6) are satisfied.

$$n_0 \cdot \sin\theta_0 = n_m \cdot \sin\theta_m \quad (5)$$

$$20[\text{nm}] < \sum_{m=1}^{m} \{(G_m \cdot \cos\theta_m) \cdot (n_m/1.46)\} \leq 160[\text{nm}] \cdot \lambda_i/785[\text{nm}] \quad (6)$$

In the expressions (4) and (6) described above, all of "20 nm", "160 nm", "785 nm", and "1.46 (a dimensionless number)" are values empirically obtained by consideration of the inventors, and are important parameters. The thickness G of the light-transmissive layer 20 is set by any one method of (i) and (ii) described above, and thus an electric field enhancement degree of the electric field enhancing element 100 of this embodiment extremely increases.

A lower limit value of the expressions (4) and (6) described above is 20 nm because it is a value empirically obtained to be verified by an experimental example described later. In addition, ($\lambda_i/785$ nm) multiplied by an upper limit value of the expressions (4) and (6) is a correction term for expressing that even when the wavelength of the excitation light is changed, each expression is completed. Further, (n/1.46) multiplied by G of the expressions (4) and (6) is a correction term for expressing that even when the refractive index of the light-transmissive layer is changed, each expression is completed. These correction terms are established by experimental examples described later.

Further, it is considered that a lower limit value in the expression (4) and (6) described above is 30 nm, 40 nm, and the like due to the following reasons. According to the structure of the electric field enhancing element 100 of this embodiment, a plurality of metallic particles 30 is disposed on the light-transmissive layer 20. When the thickness G of the light-transmissive layer 20 is below approximately 20 nm, a variation amount in a position of an enhancement degree peak in an electric field enhancing spectrum of the electric field enhancing element 100 extremely increases due to a variation in a size of the metallic particles 30. For example, as described in the following experimental examples, when the thickness G of the light-transmissive layer 20 is approximately 20 nm, a strong enhancement degree is obtained, but a peak position of an enhancement degree is sensitive to a change in a diameter of the metallic particles 30, and thus a design of an electric field enhancement degree profile of the electric field enhancing element 100 is slightly cumbersome. For this reason, on the contrary, the thickness G of the light-transmissive layer 20 may exceed 20 nm (20 nm<G), and more preferably, the thickness G of the light-transmissive layer 20 is greater than or equal to approximately 30 nm, and thus the electric field enhancing element 100 is easily designed, and it is possible to increase an allowable range of a variation in manufacturing.

Further, when the thickness G of the light-transmissive layer 20 is below approximately 40 nm, a mutual interaction between the localized surface plasmon in the vicinity of the metallic particles 30 and the propagating surface plasmon in the vicinity of the surface of the metallic layer 10 increases. As described in the following experimental examples, when the thickness G of the light-transmissive layer 20 is below approximately 40 nm, a ratio of an enhancement degree of a top of the metallic particles 30 to an enhancement degree in a bottom of the metallic particles 30 decreases. Thus, a distribution of energy for enhancing an electric field is biased to the bottom of the metallic particles 30, and thus usage efficiency of the energy of the excitation light for forming an enhanced electric field for detecting a trace substance decreases. Therefore, the thickness G of the light-transmissive layer 20 is greater than or equal to approximately 40 nm, and thus it is possible to more effectively use the energy of the excitation light for forming the enhanced electric field for detecting the trace substance. Furthermore, this will be described in "1.5. Position of Hot Spot" and the like.

1.3. Metallic Particles

The metallic particles 30 are disposed to be separated from the metallic layer 10 in the thickness direction. That is, the metallic particles 30 are disposed on the light-transmissive layer 20, and are arranged to be spatially separated from the metallic layer 10. The light-transmissive layer 20 is disposed between the metallic particles 30 and the metallic layer 10. In an example of the electric field enhancing element 100 in FIG. 1 to FIG. 4 of this embodiment, the light-transmissive layer 20 is disposed on the metallic layer 10, and the metallic particles 30 are formed thereon, and thus the metallic layer 10 and the metallic particles 30 are arranged to be separated from the light-transmissive layer in the thickness direction.

A shape of the metallic particles 30 is not particularly limited. For example, the shape of the metallic particles 30 is able to be in the shape of a circle, an ellipse, a polygon, an infinite form, or a combination thereof when projecting in the thickness direction of the metallic layer 10 and the light-transmissive layer 20 (in a plan view seen from the thickness direction), and is able to be in the shape of a circle, an ellipse, a polygon, an infinite form, or a combination thereof when projecting in a direction perpendicular to the thickness direction. In all examples of FIG. 1 to FIG. 4, the metallic particles 30 are illustrated as a cylinder having a center axis in the thickness direction of the light-transmissive layer 20, but the shape of the metallic particles 30 is not limited thereto.

A size T of the metallic particles 30 in the height direction indicates a length of a section in which the metallic particles 30 are able to be cut by a flat surface vertical to the height direction, and is greater than or equal to 1 nm and less than or equal to 100 nm. In addition, a size of the metallic particles 30 in the first direction perpendicular to the height direction indicates a length of a section in which the metallic particles 30 are able to be cut by a flat surface vertical to the first direction, and is greater than or equal to 5 nm and less than or equal to 200 nm. For example, when the shape of the metallic particles 30 is a cylinder having a center axis in the height direction, a size of the metallic particles 30 in the height direction (a height of the cylinder) is greater than or equal to 1 nm and less than or equal to 100 nm, preferably greater than or equal to 2 nm and less than or equal to 50 nm, more preferably greater than or equal to 3 nm and less than or equal to 30 nm, and further preferably greater than or equal to 4 nm and less than or equal to 20 nm. In addition, when the shape of the metallic particles 30 is a cylinder having a center axis in the height direction, a size of the metallic particles 30 in the first direction (a diameter of a bottom surface of the cylinder) is greater than or equal to 10 nm and less than or equal to 200 nm, preferably greater than or equal to 20 nm and less than or equal to 150 nm, more preferably greater than or equal to 25 nm and less than or equal to 100 nm, and further preferably greater than or equal to 30 nm and less than or equal to 72 nm.

The shape or a material of the metallic particles 30 is arbitrary insofar as the localized surface plasmon is generated due to the irradiation of the excitation light, and as the material capable of generating the localized surface plasmon due to light in the vicinity of visible light, gold, silver, aluminum, copper, platinum, an alloy thereof, and the like are able to be included.

The metallic particles 30, for example, are able to be formed by a method in which a thin film is formed by sputtering, vapor deposition, and the like, and then is patterned, a micro-contact printing method, a nanoimprint method, and the like. In addition, the metallic particles 30 are able to be formed by a colloid chemical method, and may be arranged in a position separated from the metallic layer 10 by a suitable method.

The metallic particles 30 have a function of generating the localized surface plasmon (LSP) in the electric field enhancing element 100 of this embodiment. The metallic particles 30 are irradiated with the excitation light, and thus the localized surface plasmon is able to be generated in the vicinity of the metallic particles 30. The localized surface plasmon generated in the metallic particles 30 is able to be mutually interacted (hybrid) with the propagating surface plasmon (PSP) generated in the metallic layer 10 described above under a constant condition.

1.3.1. Arrangement of Metallic Particles

As illustrated in FIG. 1 to FIG. 4, the metallic particles 30 are configured of a plurality of parallel metallic particle rows 31. The metallic particles 30 are arranged in parallel with the first direction perpendicular to the thickness direction of the metallic layer 10 in the metallic particle row 31. In other words, the metallic particle row 31 has a structure in which a plurality of metallic particles 30 is arranged in the first direction perpendicular to the height direction. When metallic particles 30 have a longitudinal shape (an anisotropic shape), the first direction in which the metallic particles 30 are arranged may not be coincident with a longitudinal direction thereof. A plurality of metallic particles 30 may be arranged in one metallic particle row 31, and the number of arranged metallic particles 30 is preferably greater than or equal to 10.

Here, a pitch of the metallic particles 30 in the first direction inside the metallic particle row 31 is defined as a first pitch P1 (refer to FIG. 2 to FIG. 4). The first pitch P1 indicates a distance between gravity centers of two metallic particles 30 in the first direction. Furthermore, when the metallic particles 30 is in the shape of a cylinder having a center axis in the thickness direction of the metallic layer 10, an interparticle distance between two metallic particles 30 inside the metallic particle row 31 is identical to a length obtained by subtracting a diameter of the cylinder from the first pitch P1.

The first pitch P1 of the metallic particles 30 in the first direction inside the metallic particle row 31 is able to be greater than or equal to 10 nm and less than or equal to 2 μm, preferably greater than or equal to 20 nm and less than or equal to 1500 nm, more preferably greater than or equal to 30 nm and less than 1000 nm, and further preferably greater than or equal to 50 nm and less than 800 nm.

The metallic particle row 31 is configured of a plurality of metallic particles 30 arranged in the first direction at the first pitch P1, and a distribution, intensity, or the like of the localized surface plasmon generated in the metallic particles 30 also depends on the arrangement of the metallic particles 30. Therefore, the localized surface plasmon mutually interacted with the propagating surface plasmon generated in the metallic layer 10 may include not only localized surface plasmon generated in single metallic particle 30, but also localized surface plasmon considering the arrangement of the metallic particles 30 in the metallic particle row 31.

As illustrated in FIG. 1 to FIG. 4, the metallic particle row 31 is arranged in parallel with the second direction intersecting with the thickness direction of the metallic layer 10 and the first direction at a second pitch P2. A plurality of metallic particle rows 31 may be arranged, and the number of arranged metallic particle rows 31 is preferably greater than or equal to 10 rows.

Here, an interval between adjacent metallic particle rows 31 in the second direction is defined as the second pitch P2. The second pitch P2 indicates a distance between gravity centers of two metallic particle rows 31 in the second direction. In addition, when the metallic particle row 31 is configured of a plurality of rows, the second pitch P2 indicates a distance between a position of a gravity center of a plurality of rows in the second direction and a position of a gravity center of a plurality of rows of the adjacent metallic particle rows 31 in the second direction.

Similar to the first pitch P1, the second pitch P2 between the metallic particle rows 31 is able to be greater than or equal to 10 nm and less than or equal to 2 μm, preferably greater than or equal to 20 nm and less than or equal to 1500 nm, more preferably greater than or equal to 30 nm and less than 1000 nm, and further preferably greater than or equal to 50 nm and less than 800 nm.

Furthermore, an angle between a line of the metallic particle row 31 extending in the first direction and a line connecting two metallic particles 30 which are closest to each other in two metallic particles 30 each belonging to the adjacent metallic particle rows 31 is not particularly limited, and may be a right angle. For example, the angle between two lines may be a right angle, or may not be a right angle. That is, when the arrangement of the metallic particles 30 seen from the thickness direction is in the shape of a two-dimensional grating having a position of the metallic particles 30 as a grating point, an irreducible basic unit grating may be in the shape of a rectangle, or may be in the shape of a parallelogram. In addition, when the angle between the line of the metallic particle row 31 extending in the first direction and the line connecting the two metallic particles 30 which are closest to each other in the two metallic particles 30 each belonging to the adjacent metallic particle rows 31 is not a right angle, a pitch between the two metallic particles 30 which are closest to each other in the two metallic particles 30 each belonging to the adjacent metallic particle rows 31 may be the second pitch P2.

1.3.2. Propagating Surface Plasmon and Localized Surface Plasmon

Figure 7:
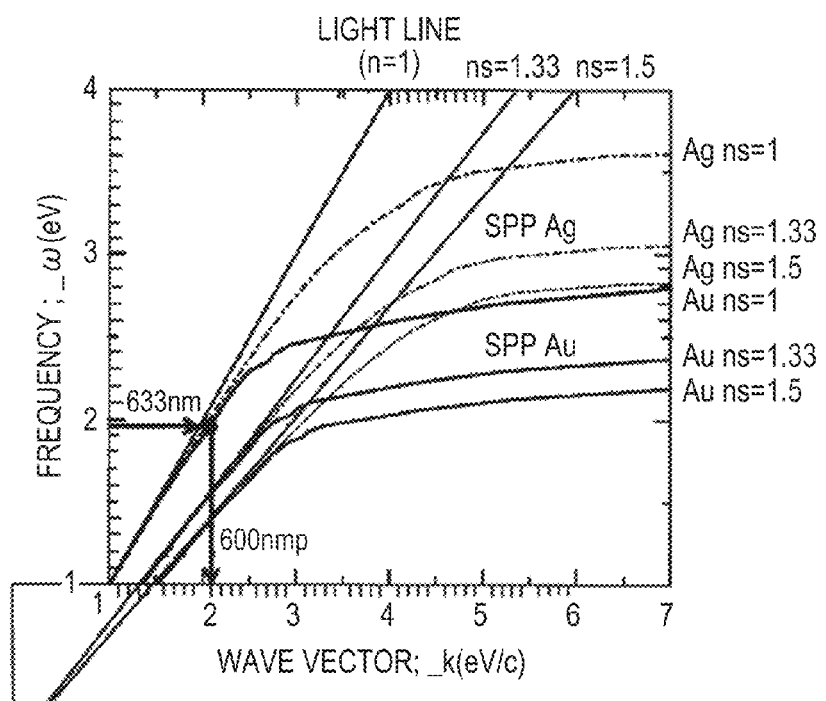
FIG. 7 is a dispersion relationship according to a refractive index in the vicinity of a metallic layer.

First, the propagating surface plasmon will be described. FIG. 7 is a graph of a dispersion relationship illustrating a dispersion curve of the excitation light, gold (a solid line), and silver (a broken line). In general, even when light is incident on a surface of metal at an incident angle θ (an irradiation angle θ) of 0 to 90 degrees, the propagating surface plasmon is not generated. For example, this is because when the metal is formed of Au, as illustrated in FIG. 7, a light line and a dispersion curve of SPP of Au do not have an intersecting point. In addition, even when a refractive index of a medium through which light passes is changed, SPP of Au is also changed according to a peripheral refractive index, and thus the light line and the dispersion curve do not have the intersecting point. In order to cause the propagating surface plasmon to have the intersecting point, a method in which a metallic layer is disposed on a prism as Kretschmann arrangement, and a wavenumber of the excitation light is increased by a refractive index of the prism, or a method in which a wavenumber of the light line is increased by a diffraction grating is used. Furthermore, FIG. 7 is a graph illustrating a so-called dispersion relationship (a vertical axis is an angular frequency ω (eV), and a horizontal axis is a wave vector k (eV/c)).

In addition, the angular frequency ω (eV) of the vertical axis in the graph of FIG. 7 has a relationship of X nm=1240/ω (eV), and is able to be converted to a wavelength. In addition, the wave vector k (eV/c) of the horizontal axis in the graph of FIG. 7 has a relationship of k (eV/c)=2π·2/λ nm/100. Therefore, for example, when a diffraction grating interval is Q, and Q is 600 nm, k is 2.09 (eV/c). In addition, the irradiation angle θ is an inclined angle from the thickness direction of the metallic layer 10 or the light-transmissive layer 20, or the height direction of the metallic particles 30 in the irradiation angle θ of the excitation light.

FIG. 7 illustrates the dispersion curve of SPP of gold (Au) and silver (Ag), and in general, when an angular frequency of the excitation light incident on the surface of the metal is ω, a speed of light in vacuum is c, a dielectric constant of the metal configuring the metallic layer 10 is E (ω), and a peripheral dielectric constant is E, the dispersion curve of SPP of the metal is given as an expression (A):

$$K_{SPP}=\omega/c[\in\cdot\in(\omega)/(\in+\in(\omega))]^{1/2} \quad (A).$$

On the other hand, the inclined angle from the thickness direction of the metallic layer 10 or the light-transmissive layer 20, or the height direction of the metallic particles 30 in the irradiation angle of the excitation light is θ, a wavenumber K of the excitation light passing through a virtual diffraction grating having an interval Q is expressed by an expression (B):

$$K=n\cdot(\omega/c)\cdot\sin\theta+a\cdot2\pi/Q \ (a=\pm1,\pm2,\dots) \quad (B),$$

and this relationship is illustrated as a straight line but not a curve on the graph of the dispersion relationship.

Furthermore, in the expression (B), n is a peripheral refractive index, and an extinction coefficient is κ, a real part $\in'$ and an imaginary part $\in''$ of a specific dielectric constant $\in$ in a frequency of light are given as $\in'=n^2-\kappa^2$, and $\in''=2n\kappa$, and when a peripheral substance is transparent, $\in$ is a real number of κ to 0, and thus $\in$ is $n^2$, and n is $\in^{1/2}$.

In the graph of the dispersion relationship, when the dispersion curve of SPP of the metal (the expression (A) described above) and the straight line of the diffracted light (the expression (B) described above) have the intersecting point, the propagating surface plasmon is excited. That is, when a relationship of $K_{SPP}=K$ is completed, the propagating surface plasmon is excited to the metallic layer 10.

Therefore, the following expression (2) is obtained from the expressions (A) and (B) described above, and it is understood that when a relationship of the expression (2) is satisfied:

$$(\omega/c)\cdot\{\in\cdot\in(\omega)/(\in+\in(\omega))\}^{1/2}=\in^{1/2}\cdot(\omega/c)\cdot\sin\theta+2a\pi/Q$$
$$(a=\pm1,\pm2,\dots) \quad (2),$$

the propagating surface plasmon is excited to the metallic layer 10. In this case, according to an example of SPP in FIG. 7, θ and m are changed, and thus a slope and/or a segment of the light line are able to be changed, and the straight line of the light line is able to intersect with the dispersion curve of SPP of Au.

Next, the localized surface plasmon will be described.

A condition in which the localized surface plasmon is generated in the metallic particles 30 by the real part of the dielectric constant is given as:

$$\text{Real}\ [\in(\omega)]=-2\in \quad (C).$$

When the peripheral refractive index n is 1, $\in=n^2-\kappa^2=1$, and thus Real $[\in(\omega)]=-2$.

Figure 8:
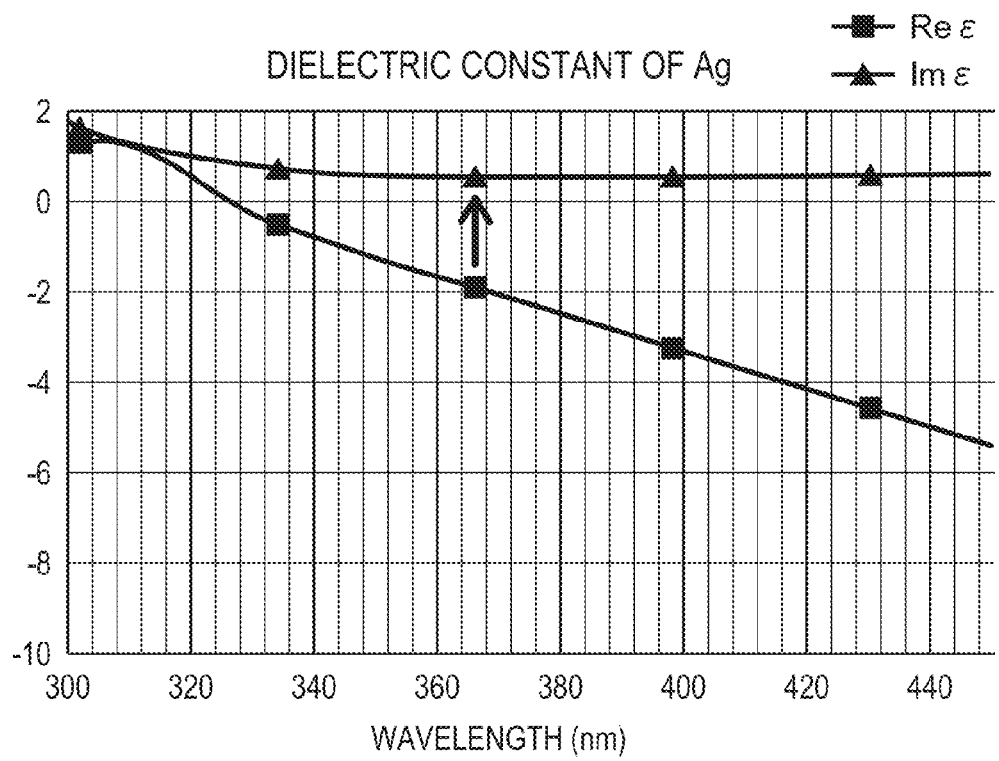
FIG. 8 is a wavelength characteristic of a dielectric constant of silver.

FIG. 8 is a graph illustrating a relationship between a dielectric constant of Ag and a wavelength. For example, the dielectric constant of Ag is as illustrated in FIG. 8, and the localized surface plasmon is excited at a wavelength of approximately 366 nm, but when a plurality of silver particles is close to a nano-order, or when silver particles and the metallic layer 10 (an Au film or the like) are arranged to be separated by the light-transmissive layer 20 (for example, SiO$_2$ or the like), an excitation peak wavelength of the localized surface plasmon is red-shifted (shifted to a long wavelength side) due to an influence of a gap thereof (the thickness G of the light-transmissive layer 20). A shift amount thereof depends on a dimension such as a diameter D of the silver particles, a thickness T of the silver particles, a particle interval between the silver particles, and the thickness G of the light-transmissive layer 20, and for example, exhibits a wavelength characteristic having a peak of the localized surface plasmon of 500 nm to 900 nm.

In addition, the localized surface plasmon is different from the propagating surface plasmon, and is plasmon which is not moved with a speed, and when plotting in the graph of the dispersion relationship, a slope is zero, that is, ω/k=0.

Figure 9:
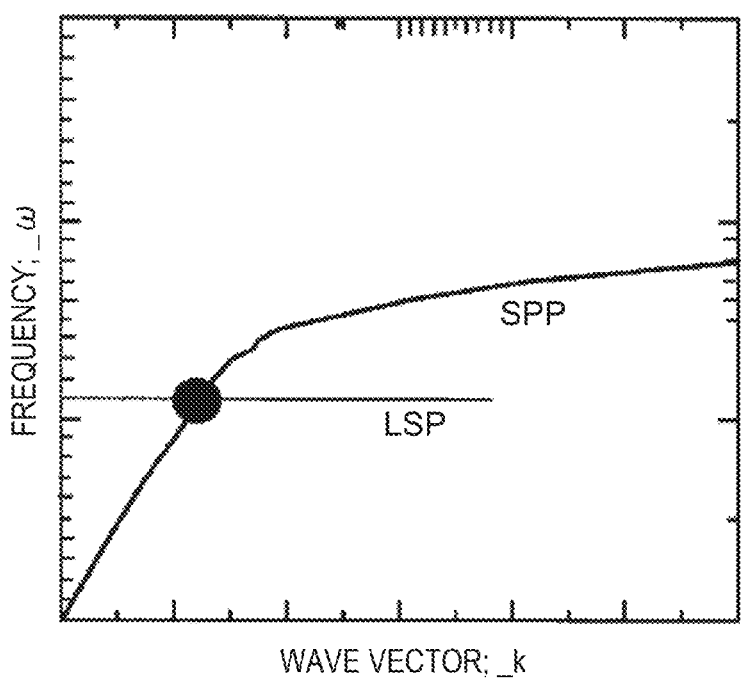
FIG. 9 is a diagram illustrating a dispersion relationship and an electromagnetic coupling between propagating surface plasmon of the metallic layer and localized surface plasmon of metallic particles.

FIG. 9 is a diagram illustrating a dispersion relationship and an electromagnetic coupling between the surface plasmon polariton (SPP) of the metallic layer 10 and the localized surface plasmon (LSP) generated in the metallic particles 30. The electric field enhancing element 100 of this embodiment electromagnetically bonds (Electromagnetic Coupling) the propagating surface plasmon and the localized surface plasmon, and thus an enhancement degree having an extremely great electric field is obtained. That is, in the electric field enhancing element 100 of this embodiment, in the graph of the dispersion relationship, the intersecting point between the straight line of the diffracted light and the dispersion curve of SPP of the metal is not set as an arbitrary point, but the metallic particles 30 which are a diffraction grating are arranged such that the straight line of the diffracted light and the dispersion curve intersect with each other in the vicinity of a point in which the greatest or a maximum enhancement degree is obtained in the localized surface plasmon generated in the metallic particles 30 (the metallic particle row 31) (refer to FIG. 7 and FIG. 9). Therefore, in the electric field enhancing element 100 of this embodiment, the localized surface plasmon (LSP) excited to the metallic particles 30, and the propagating surface plasmon (PSP) excited to a surface boundary between the metallic layer 10 and the light-transmissive layer 20 are electromagnetically and mutually interacted. Furthermore, when the propagating surface plasmon and the localized surface plasmon are electromagnetically bonded (Electromagnetic Coupling), for example, anti-crossing behavior as described in OPTICS LETTERS/Vol. 34, No. 3/Feb. 1, 2009 or the like occurs.

In other words, in the electric field enhancing element 100 of this embodiment, it is designed such that the straight line of the diffracted light passes through the vicinity of an intersecting point between the dispersion curve of SPP of the metal and the angular frequency of the excitation light (a line in parallel with the horizontal axis of LSP in the graph of the dispersion relationship in FIG. 9) in which the greatest or the maximum enhancement degree is obtained in the localized surface plasmon generated in the metallic particles 30 (the metallic particle row 31) in the graph of the dispersion relationship.

1.3.3. Second Pitch P2

As described above, the second pitch P2 between the metallic particle rows 31 may be identical to the first pitch P1, or may be different from the first pitch P1, and for example, when the excitation light is in a vertical incidence (the incident angle θ=0), primary diffracted light (a=0) is used, and the interval Q of the diffraction grating described above is adopted as the second pitch P2, an expression (C) is able to be satisfied. However, the interval Q capable of satisfying the expression (C) has a width according to an incident angle θ and an order m of diffracted light to be selected. Furthermore, in this case, it is preferable that the incident angle θ is an inclined angle from the thickness direction to the second direction, and may be an inclined angle toward a direction including a component of the first direction.

Therefore, a range of the second pitch P2 in which a hybrid between the localized surface plasmon and the propagating surface plasmon is able to occur may satisfy a relationship of an expression (D) considering that the range is in the vicinity of the intersecting point described above (a width of ±P1).

$$Q-P1 \geq P2 \geq Q+P1 \tag{D}$$

Furthermore, the second pitch P2 may satisfy a relationship of P1<P2, and may satisfy a relationship of the following expression (1).

$$P1 < P2 \leq Q+P1 \tag{1}$$

Furthermore, in general, in a case of a vertical incidence (in a case of an oblique incidence, a diffraction grating pitch passing through the intersecting point between LSP and SPP varies according to an incident angle, and thus the description thereof is inaccurate, and the vertical incidence will be described), when a value of the first pitch P1 and the second pitch P2 is smaller than the wavelength of the excitation light, intensity of the localized surface plasmon which is moved between the metallic particles 30 tends to increase, and on the contrary, when the value of the first pitch P1 and the second pitch P2 is close to the wavelength of the excitation light, intensity of the propagating surface plasmon generated in the metallic layer 10 tends to increase. Further, an electric field enhancement degree of the entire electric field enhancing element 100 depends on hot spot density (a rate of a region having a high electric field enhancement degree per unit area) (HSD), and thus HSD decreases as the value of the first pitch P1 and the second pitch P2 becomes greater. For this reason, the value of the first pitch P1 and the second pitch P2 is in a preferred range, and for example, it is preferable that the range is 60 nm≥P1≥1310 nm, and 60 nm≤P2≤1310 nm.

1.4. Surface Enhanced Raman Scattering

The electric field enhancing element 100 of this embodiment indicates a high electric field enhancement degree. Therefore, the electric field enhancing element 100 is able to be preferably used for surface enhanced Raman scattering (SERS) measurement.

In Raman scattering, when a wavelength of excitation light is $\lambda_i$, and a wavelength of scattering light is $\lambda_s$, a shift amount (cm$^{-1}$) due to the Raman scattering is given as the following expression (a).

$$\text{Amount of Raman Scattering} = (1/\lambda_i) - (1/\lambda_s) \tag{a}$$

Hereinafter, acetone will be described as an example of a target substance exhibiting a Raman scattering effect.

It is found that the acetone causes the Raman scattering in 787 cm$^{-1}$, 1708 cm$^{-1}$, and 2921 cm$^{-1}$.

According to the expression (a) described above, when the wavelength of excitation light $\lambda_i$ is 633 nm, the wavelength of stokes Raman scattering light $\lambda_s$ due to acetone is 666 nm, 709 nm, and 777 nm each corresponding to the shift amount described above. In addition, when the wavelength of excitation light $\lambda_i$ is 785 nm, each wavelength $\lambda_s$ is 837 nm, 907 nm, and 1019 nm corresponding to the shift amount described above.

In addition, there is also anti-strokes scattering, but in principle, an occurrence probability of the strokes scattering increases, and in the SERS measurement, strokes scattering in which a scattering wavelength is longer than an excitation wavelength is generally used.

On the other hand, in the SERS measurement, a phenomenon in which extremely low intensity of Raman scattering light is able to be dramatically increased by using an electric field enhancing effect due to surface plasmon is used. That is, an electric field enhancement degree $E_i$ of the wavelength of excitation light $\lambda_i$ and an electric field enhancement degree $E_s$ of the wavelength of Raman scattering light $\lambda_s$ are strong, HSD increases, and SERS intensity is proportionate to the following expression (b).

$$E_i^2 \cdot E_s^2 \cdot HSD \tag{b}$$

Here, $E_i$ represents the electric field enhancement degree of the wavelength of excitation light $\lambda_i$, $E_s$ represents the electric field enhancement degree of the wavelength of Raman scattering light $\lambda_s$, and HSD represents Hot Spot Density which is the number of hot spots per unit area.

That is, in the SERS measurement, it is preferable that a wavelength of excitation light to be used and a wavelength characteristic of Raman scattering light of a target substance to be detected are ascertained, and a wavelength of the excitation light, a wavelength of scattering light and a wavelength at a peak in an electric field enhancement degree (Reflectance) spectrum of surface plasmon are designed to be substantially coincident with one another in order that an SERS enhancement degree in proportion to the expression (b) described above is large. In addition, it is preferable that an SERS sensor has a broad peak in the electric field enhancement degree (reflectance) spectrum, and a value of a high enhancement degree.

In addition, when a surface plasmon resonance (SPR) is generated by the irradiation of the excitation light, absorption occurs due to the resonance, and the reflectance decreases. For this reason, intensity of an SPR enhanced electric field is able to be expressed by (1−r) using reflectance r. According to a relationship in which intensity of an enhanced electric field is strong as a value of the reflectance R becomes closer to zero, the reflectance is able to be used as an index of the intensity of the SPR enhanced electric field. For this reason, herein, it is considered that an enhancement degree profile (an enhancement degree spectrum) and a reflectance profile (a reflectance spectrum) are correlated with each other, and the enhancement degree profile and the reflectance profile are regarded as identical to each other on the basis of the relationship described above.

1.5. Position of Hot Spot

When the electric field enhancing element 100 of this embodiment is irradiated with the excitation light, a region having a great enhanced electric field is generated in at least an end of the metallic particles 30 on an upper surface side, that is, a corner portion of the metallic particles 30 in a side away from the light-transmissive layer 20 (hereinafter, this position is referred to as a "top", and is indicated by "t" in the drawings), and an end of the metallic particles on a lower surface side, that is, a corner portion of the metallic particles 30 on a side close to the light-transmissive layer 20 (hereinafter, this position is referred to as a "bottom", and is indicated by "b" in the drawings). Furthermore, the corner portion of the metallic particles 30 on the side away from the light-transmissive layer 20 corresponds to a head portion of the metallic particles 30, and for example, indicates a peripheral portion of a surface (a circular surface) on the side away from the light-transmissive layer 20 when the metallic particles 30 are in the shape of a cylinder having a center axis in the normal direction of the light-transmissive layer 20. In addition, the corner portion of the metallic particles 30 on the side close to the light-transmissive layer 20 corresponds to a bottom portion of the metallic particles 30, and for example, indicates a peripheral portion of a surface (a circular surface) on the side close to the light-transmissive layer 20 when the metallic particles 30 are in the shape of a cylinder having a center axis in the normal direction of the light-transmissive layer 20.

It is considered that the metallic particles 30 are arranged on the light-transmissive layer 20 into a convex shape, and thus when a target substance is close to the electric field enhancing element 100, a probability of being in contact with the top of the metallic particles 30 is greater than a probability of being in contact with the bottom of the metallic particles 30.

In such a consideration, when focusing on a condition in which an electric field enhancement degree increases in the top of the metallic particles 30, it is possible to determine a range of the thickness G of the light-transmissive layer 20 described above. That is, as described above, the electric field enhancing element 100 of this embodiment includes the metallic layer 10, the light-transmissive layer 20 which is disposed on the metallic layer 10 and transmits the excitation light, and a plurality of metallic particles 30 which is disposed on the light-transmissive layer 20, and is arranged in the second direction intersecting with the first direction and the first direction, and at the time of the irradiation of the excitation light, the localized surface plasmon excited to the metallic particles 30 (neighborhood) and the propagating surface plasmon excited to the surface boundary (neighborhood) between the metallic layer 10 and the light-transmissive layer 20 are electromagnetically and mutually interacted. Then, by selecting the thickness G of the light-transmissive layer 20 according to at least one of the conditions (i) and (ii) described in "1.2. Light-Transmissive Layer", it is possible to extremely increase an electric field enhancement degree in the top of the metallic particles 30.

In addition, according to the structure of the electric field enhancing element 100 of this embodiment, a plurality of metallic particles 30 is disposed on the light-transmissive layer 20. As described above, when the thickness G of the light-transmissive layer 20 is below approximately 40 nm, the mutual interaction between the localized surface plasmon in the vicinity of the metallic particles 30 and the propagating surface plasmon in the vicinity of the surface of the metallic layer 10 increases, and the ratio of the enhancement degree in the top of the metallic particles 30 to the enhancement degree in the bottom of the metallic particles 30 decreases. That is, the distribution of the energy for enhancing the electric field is biased to the bottom of the metallic particles 30.

It is considered that when the thickness G of the light-transmissive layer 20 is below approximately 40 nm, the electric field enhancement degree in the top of the metallic particles 30 with which the target substance is easily in contact relatively decreases even when a total electric field enhancement degree is not changed, and efficiency of enhancing the electric field of the electric field enhancing element 100 decreases. From such a viewpoint, when the lower limit value of the thickness G of the light-transmissive layer 20 is set according to at least one of the conditions (i) and (ii), and is greater than or equal to 40 nm, the ratio of the intensity of the localized surface plasmon (LSP) excited to the upper surface side (the top) of the metallic particles 30 to the intensity of the localized surface plasmon excited to the lower surface side (the bottom) of the metallic particles 30 is constant regardless of the thickness G of the light-transmissive layer 20, and thus it is possible to increase usage efficiency of the energy of enhancing the electric field.

Furthermore, here, "constant" includes a case where a specific value does not vary, a case where the specific value varies in a range of ±10%, and preferably, a case where the specific value varies in a range of ±5%.

1.6. Excitation Light

The wavelength of the excitation light incident on the electric field enhancing element 100 generates the localized surface plasmon (LSP) in the vicinity of the metallic particles 30, and the wavelength of the excitation light is not limited insofar as at least one relationship of the conditions (i) and (ii) described in "1.2. Light-Transmissive Layer" is able to be satisfied, and is able to be an electromagnetic wave including ultraviolet ray, visible light, and infrared ray. The excitation light, for example, is able to be at least one of linearly polarized light polarized in the first direction, linearly polarized light polarized in the second direction, and circularly polarized light. According to this, it is possible to obtain an extremely great enhancement degree of light by the electric field enhancing element 100.

Furthermore, when the electric field enhancing element 100 is used as the SERS sensor, linearly polarized light polarized in the first direction, linearly polarized light polarized in the second direction, and circularly polarized light are suitably used in combination as the excitation light, and the number of enhancement degree peaks in the electric field enhancing spectrum, a size, and a shape (a width) may be adjusted to the wavelength of excitation light $\lambda_i$, and the wavelength of Raman scattering light $\lambda_s$ of the target substance.

The electric field enhancing element 100 of this embodiment has the following characteristics. The electric field enhancing element 100 of this embodiment is able to enhance light to an extremely high enhancement degree on the basis of plasmon excited by the light irradiation. The electric field enhancing element 100 of this embodiment has high enhancement degree, and thus for example, in a field such as medical treatment and health, environment, food, and public safety, a biologically-relevant substance such as a bacterium, a virus, a protein, a nucleic acid, and various antigens and antibodies, and various compounds including inorganic molecules, organic molecules, and high molecules are able to be used for a sensor for rapidly and simply performing detection with high sensitivity and high accuracy. For example, an antibody is bonded to the metallic particles 30 of the electric field enhancing element 100 of this embodiment, an enhancement degree at this time is obtained, and presence or absence of the antigen or an amount are able to be inquired on the basis of a change in a peak wavelength of an enhancement degree when a antigen is bonded to the antibody, or a change in reflectance of a wavelength which is set to the vicinity of the peak wavelength. In addition, by using the enhancement degree of the light in the electric field enhancing element 100 of this embodiment, it is possible to enhance the Raman scattering light of the trace substance.

2. Analysis Apparatus

An analysis apparatus of this embodiment includes the electric field enhancing element described above, a light source, and a detector. Hereinafter, a case where the analysis apparatus is a Raman spectroscopic device will be described as an example.

Figure 10:
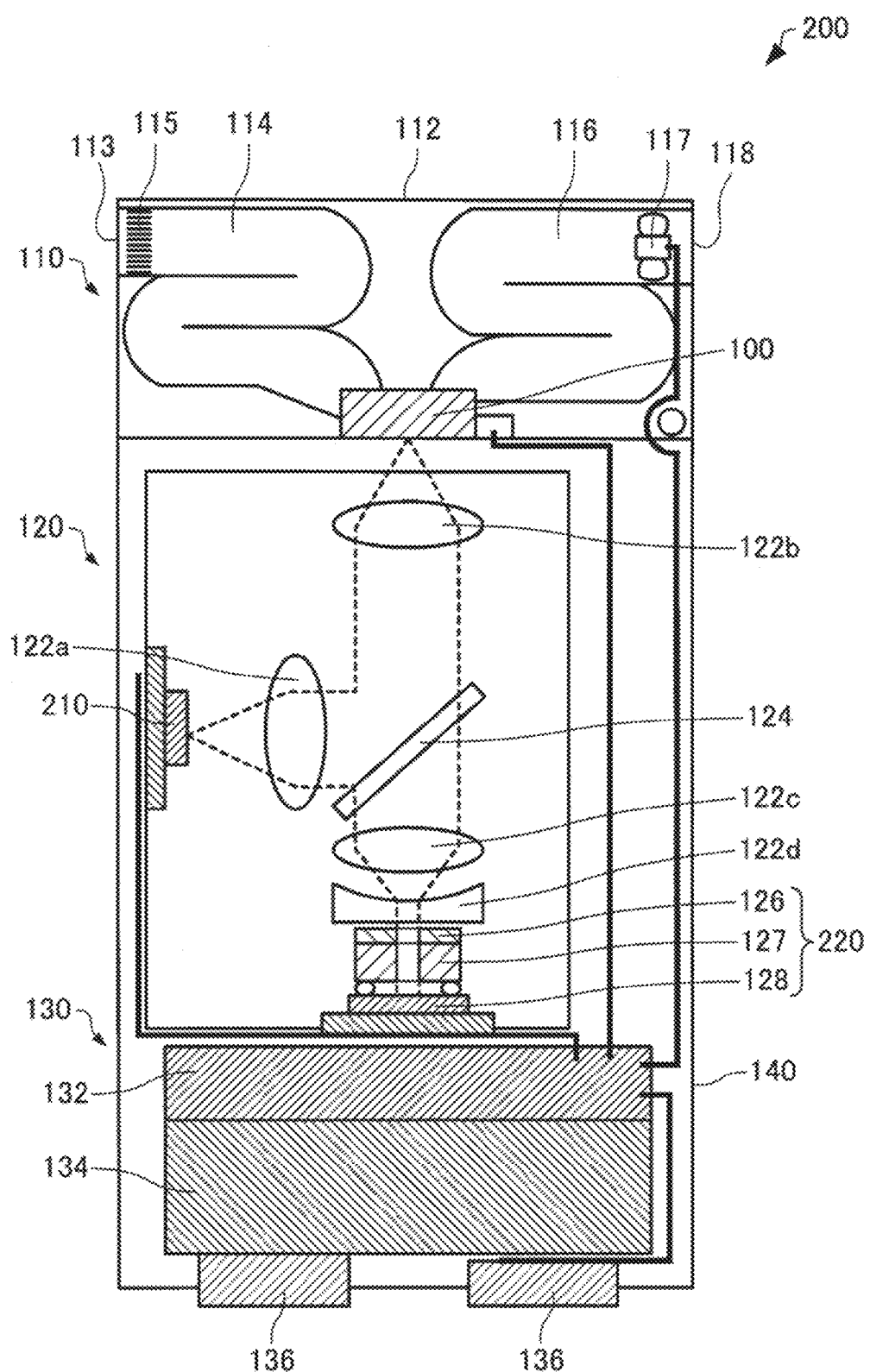
FIG. 10 is a schematic view of an analysis apparatus according to the embodiment.

FIG. 10 is a diagram schematically illustrating a Raman spectroscopic device 200 according to this embodiment. The Raman spectroscopic device 200 detects and analyzes Raman scattering light from a target substance (qualitative analysis and quantitative analysis), and as illustrated in FIG. 7, includes a housing 140 containing alight source 210, a gaseous sample holding unit 110, a detection unit 120, a control unit 130, a detection unit 120, and a control unit 130. The gaseous sample holding unit 110 includes the electric field enhancing element. Hereinafter, an example including the electric field enhancing element 100 described above will be described.

The gaseous sample holding unit 110 includes the electric field enhancing element 100, a cover 112 covering the electric field enhancing element 100, a suction flow path 114, and a discharge flow path 116. The detection unit 120 includes the light source 210, lenses 122a, 122b, 122c, and 122d, a half mirror 124, and a light detector 220. The control unit 130 includes a detection control unit 132 controlling the light detector 220 by processing a signal detected in the light detector 220, and an electric power control unit 134 controlling an electric power or a voltage of the light source 210 or the like. The control unit 130, as illustrated in FIG. 7, may be electrically connected to a connection unit 136 for being connected to the outside.

In the Raman spectroscopic device 200, when a suction mechanism 117 disposed in the discharge flow path 116 is operated, the inside of the suction flow path 114 and the discharge flow path 116 is negatively pressurized, and a gaseous sample including the target substance which is a detection target is suctioned from a suction port 113. A dust removing filter 115 is disposed in the suction port 113, and thus comparatively large dust, a part of water vapor, or the like is able to be removed. The gaseous sample is discharged from a discharge port 118 through the suction flow path 114 and the discharge flow path 116. When the gaseous sample passes through these paths, the gaseous sample is in contact with the metallic particles 30 of the electric field enhancing element 100.

The suction flow path 114 and the discharge flow path 116 have a shape in which light from the outside is not incident on the electric field enhancing element 100. Accordingly, light other than the Raman scattering light which is noise is not incident on the electric field enhancing element 100, and thus it is possible to improve an S/N ratio of the signal. A material configuring the flow paths 114 and 116, for example, is a material by which light is rarely reflected or a color.

The suction flow path 114 and the discharge flow path 116 have a shape in which fluid resistance with respect to the gaseous sample decreases. Accordingly, high sensitive detection is able to be performed. For example, the flow paths 114 and 116 have a smooth shape in which a corner portion is as fully eliminated as possible, and thus it is possible to prevent the gaseous sample from being accumulated in the corner portion. As the suction mechanism 117, for example, a fan motor or a pump of static pressure or air volume according to flow path resistance is used.

In the Raman spectroscopic device 200, the light source 210 irradiates the electric field enhancing element 100 with the excitation light. The light source 210 is arranged such that at least one of light linearly polarized in the first direction of the electric field enhancing element 100 (a direction in parallel with the metallic particles 30, and an extending direction of the metallic particle row 31) (linearly polarized light in the same direction as the first direction), light linearly polarized in the second direction, and circularly polarized light is able to be emitted. Though it is not illustrated, the incident angle θ of the excitation light emitted from the light source 210 may be suitably changed according to an excitation condition of the surface plasmon of the electric field enhancing element 100. The light source 210 may be disposed on a goniometer (not illustrated) or the like.

The light emitted by the light source 210 is identical to the light described in "1.6. Excitation Light". Specifically, as the light source 210, a light source in which a wavelength select element, a filter, a polarizer, and the like are suitably disposed in a semiconductor laser, a gas laser, a halogen lamp, a high-pressure mercury lamp, a xenon lamp, and the like is able to be used as an example.

The light emitted from the light source 210 is focused on the lens 122a, and is incident on the electric field enhancing element 100 through the half mirror 124 and the lens 122b. SERS light is emitted from the electric field enhancing element 100, and the light reaches the light detector 220 through the lens 122b, the half mirror 124, and the lenses 122c and 122d. That is, the light detector 220 detects the light emitted from the electric field enhancing element 100. The SERS light includes Rayleigh scattering light having a wavelength identical to an incident wavelength from the light source 210, and thus the Rayleigh scattering light may be removed by a filter 126 of the light detector 220. The light from which the Rayleigh scattering light is removed is received by a light receiving element 128 as the Raman scattering light through a spectroscope 127 of the light detector 220. As the light receiving element 128, for example, a photodiode or the like is used.

The spectroscope 127 of the light detector 220, for example, is formed of an etalon or the like using a Fabry-Perot resonance, and is able to change a pass wavelength bandwidth. A Raman spectrum specific to the target substance is obtained by the light receiving element 128 of the light detector 220, and for example, the obtained Raman spectrum and data stored in advance are collated with each other, and thus it is possible to detect signal intensity of the target substance.

Furthermore, the Raman spectroscopic device 200 is not limited to the example described above insofar as the Raman spectroscopic device 200 includes the electric field enhancing element 100, the light source 210, and the light detector 220, the target substance is adsorbed by the electric field enhancing element 100, and the Raman scattering light is able to be acquired.

In addition, as in a Raman spectroscopic method according to this embodiment described above, when the Rayleigh scattering light is detected, the Raman spectroscopic device 200 may disperse the Rayleigh scattering light and the Raman scattering light by a spectroscope without having the filter 126.

The Raman spectroscopic device 200 includes the electric field enhancing element 100 described above. According to this Raman spectroscopic device 200 (an analysis apparatus), an extremely high enhancement degree is obtained in an enhancement degree (reflectance) spectrum, and it is possible to detect and analyze the target substance with high sensitivity. In addition, a position in which a high enhancement degree is obtained in the electric field enhancing element 100 provided in the Raman spectroscopic device 200 is positioned at least on the upper surface side (the top) of the metallic particles 30, and the target substance is easily in contact with the position, and thus it is possible to detect and analyze the target substance with high sensitivity.

In addition, this Raman spectroscopic device sets the thickness G of the light-transmissive layer 20 of the electric field enhancing element 100 according to at least one of the conditions (i) and (ii) described in "1.2. Light-Transmissive Layer", and thus it is possible to increase an allowable range of a variation in manufacturing by setting the thickness G of the light-transmissive layer 20 to be greater than or equal to approximately 20 nm.

Further, according to this Raman spectroscopic device 200, the electric field enhancing element 100 in which a ratio of intensity of the localized surface plasmon excited to the lower surface side (the bottom) of the metallic particles 30 to intensity of the localized surface plasmon (LSP) excited to the upper surface side (the top) of the metallic particles is constant regardless of the thickness G of the light-transmissive layer 20 is used, and thus usage efficiency of energy of enhancing an electric field is high.

3. Electronic Device

Figure 11:
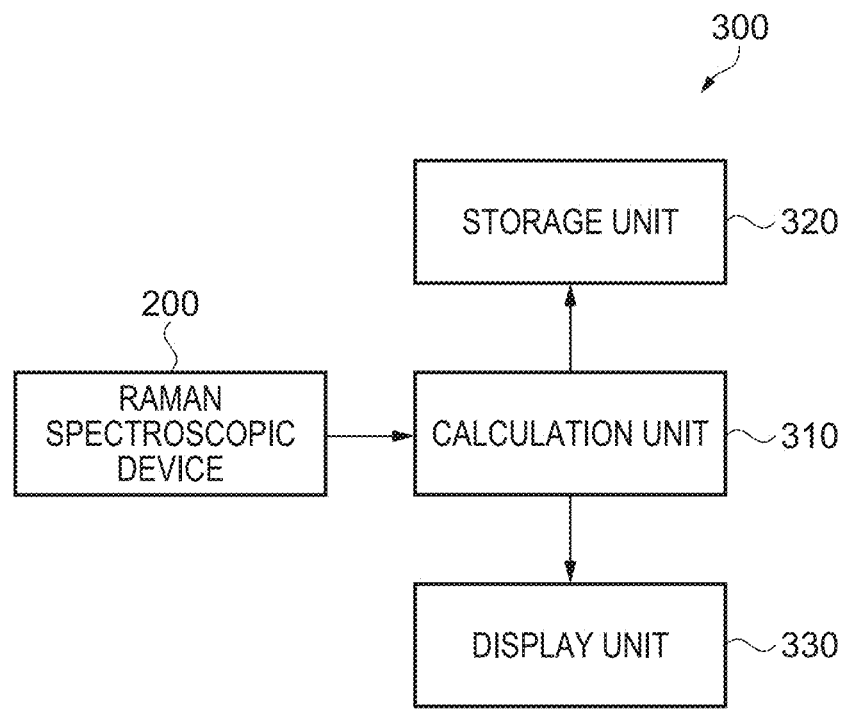
FIG. 11 is a schematic view of an electronic device according to the embodiment.

Next, an electronic device 300 according to this embodiment will be described with reference to the drawings. FIG. 11 is a diagram schematically illustrating the electronic device 300 according to this embodiment. The electronic device 300 is able to include the analysis apparatus (the Raman spectroscopic device). Hereinafter, as the analysis apparatus, an example including the Raman spectroscopic device 200 described above will be described as an example.

The electronic device 300, as illustrated in FIG. 11, includes the Raman spectroscopic device 200, a calculation unit 310 which calculates medical health information on the basis of detection information from the light detector 220, a storage unit 320 which stores the medical health information, and a display unit 330 which displays the medical health information.

The calculation unit 310, for example, is a personal computer or a personal digital assistant (PDA), and receives detection information (a signal or the like) transmitted from the light detector 220. The calculation unit 310 calculates the medical health information on the basis of the detection information from the light detector 220. The calculated medical health information is stored in the storage unit 320.

The storage unit 320, for example, is semiconductor memory, a hard disk drive, or the like, and may be configured to be integrated with the calculation unit 310. The medical health information stored in the storage unit 320 is transmitted to the display unit 330.

The display unit 330, for example, is configured by a display plate (a liquid crystal monitor or the like), a printer, an illuminator, a speaker, and the like. The display unit 330 displays or activates an alarm on the basis of the medical health information or the like calculated by the calculation unit 310 such that a user is able to recognize contents thereof.

As the medical health information, information relevant to presence or absence or an amount of at least one biologically-relevant substance selected from a group consisting of a bacterium, a virus, a protein, a nucleic acid, and an antigen and antibody, or at least one compound selected from inorganic molecules and organic molecules is able to be included.

The electronic device 300 includes the Raman spectroscopic device 200 described above. For this reason, in the electronic device 300, detection of a trace substance is able to be more efficiency performed with high sensitivity, and it is possible to provide medical health information with high accuracy.

For example, the electric field enhancing element is able to be used as an affinity sensor or the like which detects presence or absence of adsorption of a substance such as presence or absence of adsorption of an antigen in an antigen-antibody reaction. In the affinity sensor, white light is incident on the sensor, a wavelength spectrum is measured by a spectroscope, and a shift amount of a surface plasmon resonance wavelength due to adsorption is detected, and thus adsorption of a detection substance with respect to a sensor chip is able to be detected with high sensitivity.

4. Experimental Example

Hereinafter, aspects of the invention will be further described by using experimental examples, but the invention is not limited to the following examples.

Figure 12:
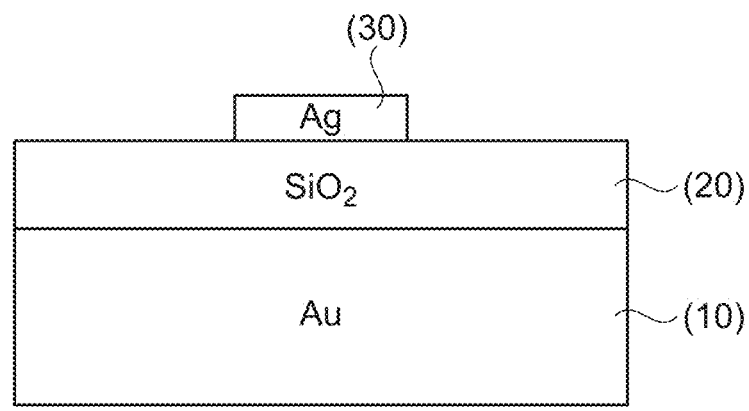
FIG. 12 is a schematic view of a model according to an experimental example.

In each experimental example, a model schematically illustrated in FIG. 12 is used. As a metallic layer which is sufficiently thick to the extent that light is not transmitted, a gold (Au) layer is used, as a light-transmissive layer, a $SiO_2$ layer having a refractive index of 1.46 is formed on the metallic layer (gold), and as metallic particles, cylindrical silver is formed on the light transmissive layer at a constant cycle, and thus a Gap type Surface Plasmon Polariton (GSPP) model is formed. Furthermore, a material of the metallic layer and the metallic particles is not limited, insofar as metal in which a real part of a dielectric constant negatively increases, and an imaginary part is smaller than the real part in a wavelength region of the excitation light is used, plasmon is able to be generated. Furthermore, $SiO_2$ is formed on the metallic layer of gold as the light-transmissive layer, and silver or gold is formed at a predetermined pitch as the metallic particles, thus a model is formed, and as a diameter of the metallic particles, a size in which a mutual interaction between LSP and PSP increases is selected.

Parameter or the Like of Calculation Model

In a graph or the like illustrated as each experimental example, for example, a signage such as "X180Y780" is used. "X180Y780" indicates that metallic particles are arranged in the first direction (an X direction) at a pitch of 180 nm (the first pitch P1) and in the second direction (a Y direction) at a pitch of 780 nm (the second pitch P2).

In addition, when a character such as "D" and "T" is applied to a numerical value, it indicates that the metallic particles used in the model are in the shape of a cylinder having a diameter D and a height T. In addition, when a symbol "G" is further applied to the numerical value, it indicates that the thickness G of the light-transmissive layer is the numerical value nm described above. In addition, a Gap thickness in the horizontal axis of the graph or the like indicates the thickness G of the light-transmissive layer. Further, when the numerical value, for example, is written with a range such as "20 to 100", it indicates that calculation is performed by adopting a continuous or infrequent (discrete) value in the range of the numerical value described above on calculation in the range described above.

Further, "Ag" or "AG" in the drawings indicates that a material of a configuration of focus is silver, and "Au" or "AU" indicates that a material of a configuration of focus is gold. In addition, "@" indicates "in a wavelength followed by @", and for example, "SQRT_@815 nm" indicates SQRT in a wavelength of 815 nm.

Outline of Calculation

The calculation is performed by using FDTD soft Full-WAVE manufactured by Rsoft (currently, Cybernet Systems Co., Ltd.). In addition, in each experimental example, near-field properties and/or far-field properties are obtained. As an FDTD calculation condition of the near-field properties, a 1 nm mesh even in XY directions, a grid grating (GG) of 1 nm to 5 nm in a Z direction (calculation time cT=10 μm), or GG of 2 nm to 10 nm in XYZ directions (calculation time cT=7 μm) is used. In addition, a condition of the used mesh will be described in each experimental example, and for example, "XY1Z1-5nmGG" indicates "XY1nmZ1-5 nm. Grid Grading", and "2-10nmGG" indicates "XYZ2-10 nm Grid Grading". The peripheral refractive index $n_0$ of the metallic particles is 1. In addition, the excitation light is in a vertical incidence from the thickness direction (Z) of the light-transmissive layer, and is linearly polarized light from the X direction (the first direction).

In an enhancing position (a hot spot), two components of electric fields $E_x$ and $E_z$ are formed, and thus an entire enhancement degree in the following experimental examples is expressed by SQRT ($E_x^2+E_z^2$). Here, $E_x$ represents intensity of an electric field in a polarization direction (the first direction) of incident light, and $E_z$ indicates electric field intensity in the thickness direction. Furthermore, in this case, the electric field intensity in the second direction is small, and thus it is not considered. In addition, hereinafter, SQRT ($E_x^2+E_z^2$) is simply referred to as "SQRT".

In addition, when the surface plasmon resonance (SPR) is generated due to the irradiation of the excitation light, absorption occurs due to the resonance, and thus reflectance decreases. For this reason, intensity in an SPR enhanced electric field is able to be expressed by (1−r) using reflectance r. According to a relationship in which intensity in an enhanced electric field is strong as a value of the reflectance r becomes closer to zero, the reflectance is used as an index of the square of the intensity (SQRT) in the SPR enhanced electric field.

In an FDTD calculation condition of the far-field properties, a monitor is disposed away from an element, pulse light having a center wavelength of 0.5 μm is incident as the excitation light, and a wavelength characteristic of the reflectance is acquired. According to this method, a minimum value (the smallest value) of the reflectance indicates a greatest value of an enhancement degree, and a wavelength having a peak at which an enhancement degree is maximized is also able to be acquired. In addition, the far-field properties are an integration value of the near-field properties in a hot spot of each portion, and in general, a result which is approximately identical to that of the near-field properties is able to be obtained. The far-field properties are mainly acquired at 2 nmGG to 10 nmGG, and a calculation time cT is 32.7 μm. Furthermore, in the far-field properties, when an abnormal value depending on a mesh size occurs, the mesh size is 1 nmGG to 5 nmGG, and the far-field properties are recalculated.

On calculation, the incident light of the linearly polarized light in the X direction is used, for example, "X120Y600" indicates that when the pitch P1 is 120 nm, and the pitch P2 is 600 nm, the result is equivalent to the result due to the incident light of the linearly polarized light in the "first direction", and "X600Y120" indicates that when the pitch P1 is 120 nm, and a row pitch P2 is 600 nm, the result is equivalent to the result due to the incident light of the linearly polarized light in the "second direction".

In addition, for convenience of description, a model in which one of the XY directions such as X180Y780 and X780Y180 is shorter than the other in a length in the vicinity of the wavelength of the excitation light is referred to as a 1 line model, a case where the excitation light polarized in the X direction (the first direction) is incident in the 1 line model, that is, X180Y780 (linear polarization in a direction along a direction in which the pitch is short) is written as "PSPILSP" or simply written as "I", and a case where the excitation light polarized in the Y direction (the second direction) is incident (linear polarization in a direction along a direction in which the pitch is long) is written as "PSP//LSP" or simply written as "//".

4.1. Experimental Example 1

Shift of Peak Wavelength with respect to Variation in Size of Metallic Particles of One Line⊥Model It is difficult to completely exclude a variation in a size of the metallic particles of the electric field enhancing element in manufacturing the element. The inventors have prepared and analyzed a plurality of electric field enhancing elements including metallic particles having a diameter of 150 nm by using an electron beam drawing device (EB), and have found that a distribution (a variation) of a standard deviation σ=5 nm occurs in the diameter of the metallic particles. That is, it has been found that as a premise of this experimental example, that is, as the diameter of the metallic particles, a difference between the greatest diameter and the smallest diameter in average is approximately 10 nm.

One Line⊥Model

First, as a model for an excitation wavelength of 633 nm, a model in which the metallic layer is gold (Au) having a thickness of 150 nm, the light-transmissive layer is $SiO_2$ of 10 nm to 50 nm, the metallic particles are silver (Ag) of 80-90D30T and are arranged in X140Y600 is calculated. This model is briefly expressed by X140Y600_80-90D30T_AG. A result in which the refractive index of the light-transmissive layer is 1.46, the thickness (the gap G) of the light-transmissive layer is changed from 10 nm to 50 nm at 10 nm intervals, and thus wavelength dependent properties (a reflectance spectrum) of the reflectance are acquired is illustrated in FIGS. 13A-C.

A condition of the excitation light is a vertical incident, and a polarization direction is the X direction. In this model, a hybrid mode in which LSP is generated in the X direction, PSP is generated in the Y direction occurs, anti-crossing behavior does not occur, and thus a peak indicating one minimum value in the reflectance spectrum is observed.

Figure 13A:
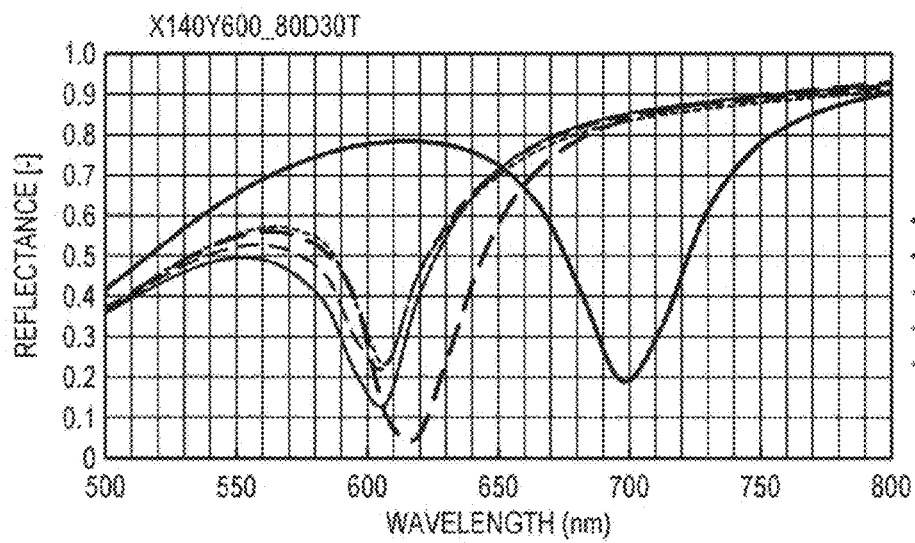
FIGS. 13A-C are reflectance spectra of the model according to the experimental example.
Figure 13B:
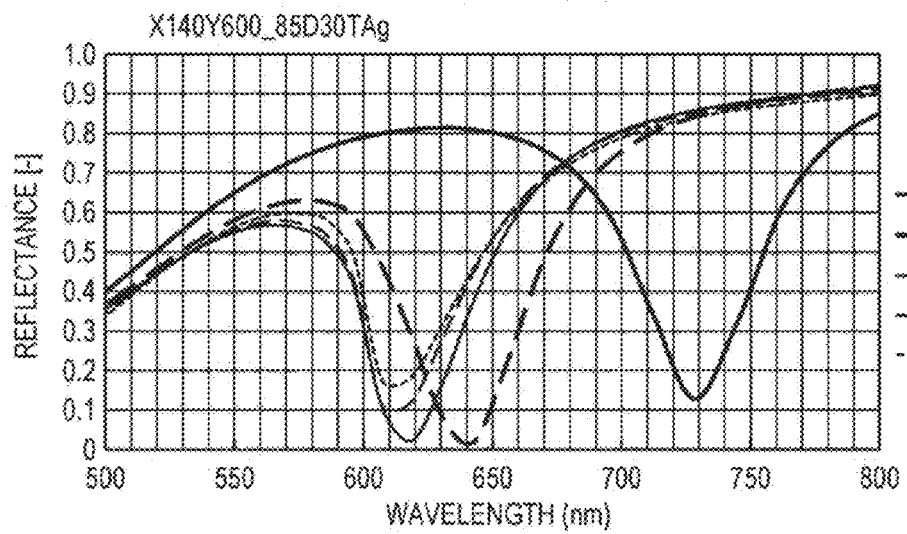
Figure 13C:
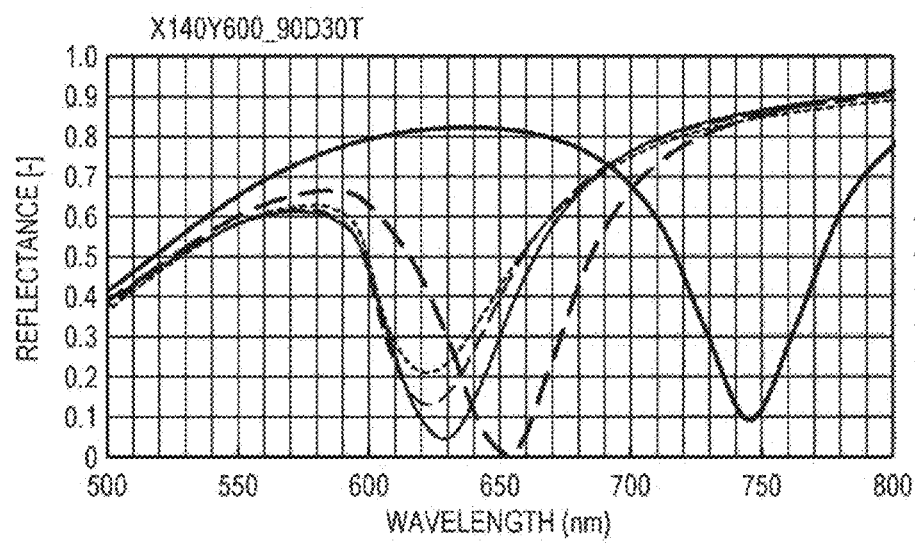

From FIGS. 13A-C, it is found that when the diameter of the metallic particles is changed to be 80 nm, 85 nm, and 90 nm, a wavelength of a minimum value in a reflectance spectrum of a model of 10G is greatly red-shifted to 700 nm, 730 nm, and 745 nm. In addition, it is found that a wavelength of a reflectance minimum value of a model of 20G is red-shifted to 615 nm, 640 nm, and 652 nm even though a shift amount is small compared to the case of 10G.

In contrast, it is found that when the diameter of the metallic particles is changed to 80 nm, 85 nm, and 90 nm, a wavelength of a reflectance minimum value of a model of 30G is red-shifted to 605 nm, 620 nm, and 628 nm which are extremely small shift amounts, and in models of 40G and 50G, a wavelength of a reflectance minimum value is rarely changed.

From these results, it is found that when the thickness of the light-transmissive layer is less than or equal to 20 nm, the wavelength of the minimum value of the reflectance is sensitively changed according to the change in the diameter of the metallic particles, when the thickness of the light-transmissive layer is greater than or equal to 30 nm, the wavelength is insensitive to the change in the diameter of the metallic particles, and when the thickness of the light-transmissive layer is greater than or equal to 40 nm, the wavelength is rarely changed according to the change in the diameter of the metallic particles. For this reason, it is found that the thickness G of the light-transmissive layer is from approximately 30 nm to approximately 40 nm or more, and thus when a variation occurs in the diameter of the metallic particles, it is difficult to change the wavelength of the minimum value of the reflectance, and it is possible to increase an allowable range of a variation in manufacturing.

Next, as a model of excitation light of 785 nm, a reflectance spectrum of the model in a dimension of one line X180Y780 is acquired. In this model, it is considered that in order to set a peak wavelength to be approximately 785 nm in AG and AU, a diameter of AG is larger than a diameter of AU, and in contrast, the diameter of AU is smaller than the diameter of AG. In this model, a hybrid mode in which LSP is generated in the X direction, and PSP is generated in the Y direction occurs, anti-crossing behavior does not occur, and thus a peak indicating one minimum value in the reflectance spectrum is observed.

Figure 14A:
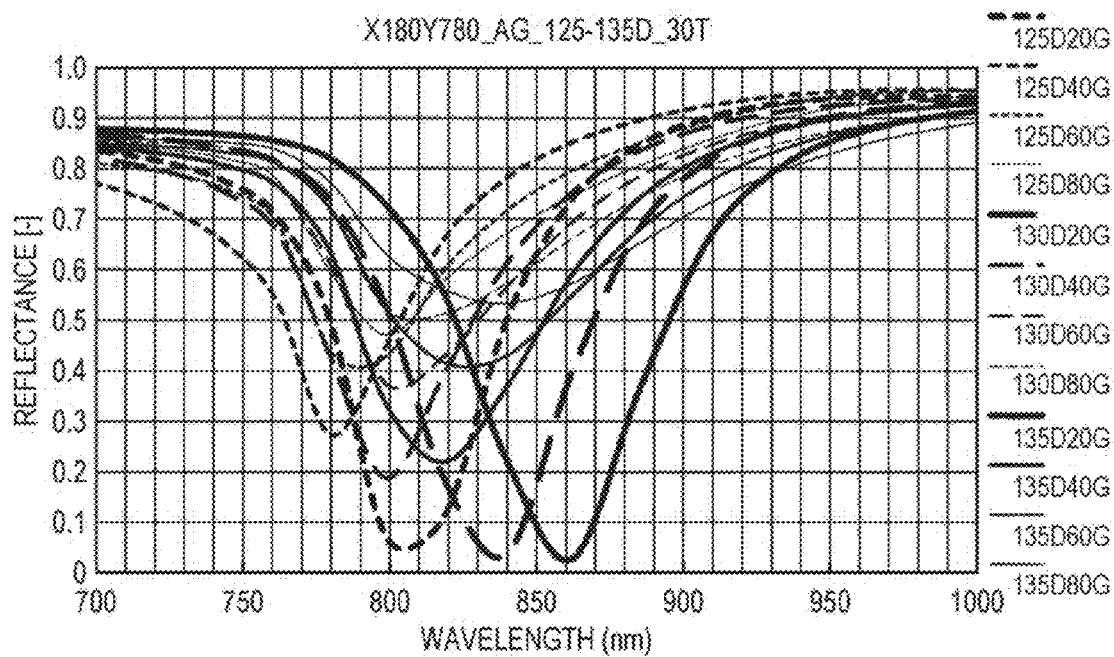
FIGS. 14A and B are reflectance spectra of the model according to the experimental example.
Figure 14B:
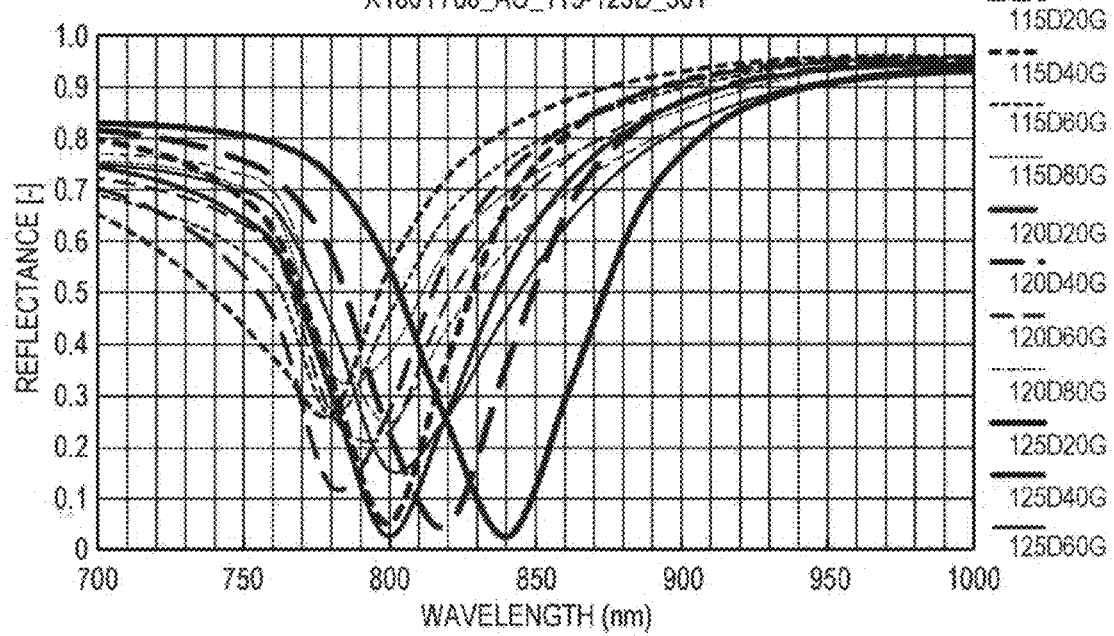

FIGS. 14A and B illustrate a wavelength characteristic (a reflectance spectrum) of reflectance of one line_X180Y780_125-135D30T_AG_20-80G and one line_X180Y780_115-125D30T_AU_20-80G.

It is found that when the thickness (G) of the light-transmissive layer is 20 nm, the diameter of the metallic particles is changed to 10 nm, and thus when the metallic particles are silver (AG), the diameter of the metallic particles is red-shifted to 55 nm, and when the metallic particles are gold (AU), the diameter of the metallic particles is red-shifted to 40 nm.

Whereas, it is found that the minimum value of the reflectance rises (increases) as the thickness (G) of the light-transmissive layer becomes thicker as 40 nm, 60 nm, and 80 nm, but for example, the wavelength of the minimum value of the reflectance is 35 nm according to the change in the diameter of 10 nm in case of Ag of 60G, the wavelength is 20 nm in case of Au of 60G, and a change amount of the wavelength of the minimum value of the reflectance decreases by approximately 20 nm compared to a case of 20G.

Therefore, from this result, it is found that when the thickness of the light-transmissive layer is less than or equal to 20 nm in a case that the metallic particles are Ag or Au, the wavelength of the minimum value of the reflectance is sensitively changed according to the change in the diameter of the metallic particles, and when the thickness is greater than or equal to 40 nm, the wavelength of the minimum value of the reflectance is insensitively changed according to the change in the diameter of the metallic particles. For this reason, it is found that the thickness G of the light-transmissive layer is from approximately 30 nm to approximately 40 nm or more, and thus when a variation occurs in the diameter of the metallic particles, it is difficult to change the wavelength of the minimum value of the reflectance, and it is possible to increase an allowable range of a variation in manufacturing.

Figure 15:
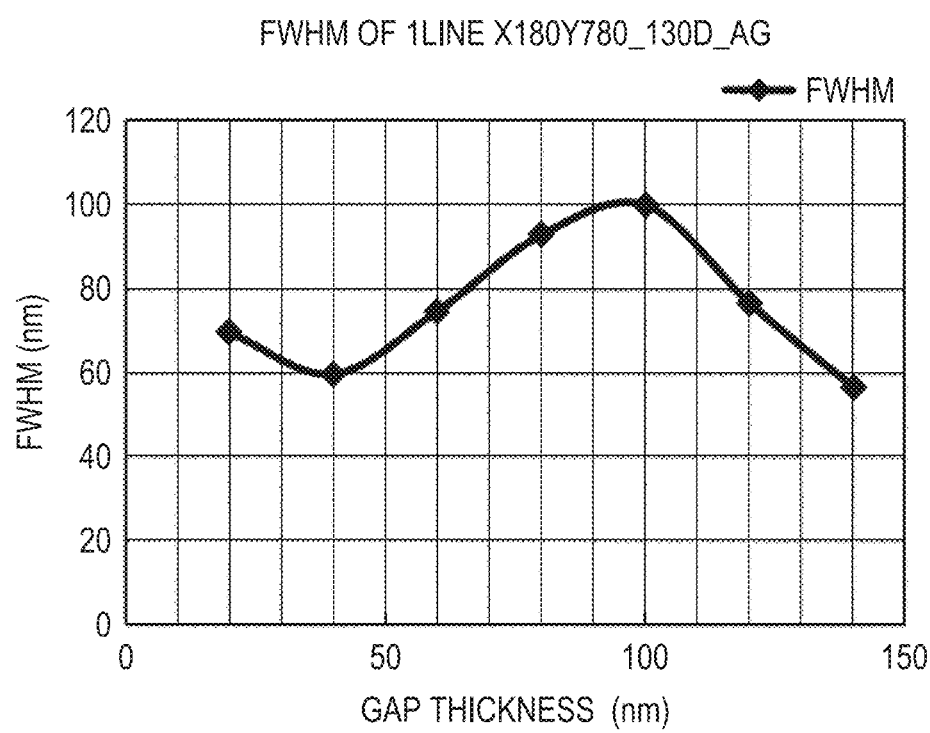
FIG. 15 is a graph illustrating light-transmissive layer thickness dependence of FWHM of the reflectance spectrum of the model according to the experimental example.

FIG. 15 is a graph illustrating a relationship between a half-value width (a half-value full-width) of a minimum peak in a reflectance spectrum of one line_X180Y780_130D30T_AG and the thickness (G) of the light-transmissive layer. In calculation of FIG. 15, a mesh of 1 GG to 5 GG is used. In addition, the half-value width is measured with respect to a downward peak, and is illustrated by "FWHM" in the drawings. FWHM is an acronym of Full Width at Half Maximum, and herein, Maximum corresponds to a minimum value.

From FIG. 15, it is found that the thickness G of the light-transmissive layer exceeding the half-value width (FWHM) >60 nm is in a range of 20 nm≥G≥140 nm. Further, it is found that when the thickness G of the light-transmissive layer is 100 nm, the half-value width exhibits broad properties of 100 nm. In Raman spectroscopy measurement, when the half-value width is wide, it is effective by the following reasons.

In the Raman scattering wavelength $\lambda_s$ and in the wavelength of excitation light $\lambda_i$, a value of $(\lambda_s-\lambda_i)$ is able to cover to 100 nm when the wavelength of the excitation light is 785 nm, the value is able to cover a Raman shift in a range up to 1450 cm$^{-1}$.

Next, in the one line_X180Y780_130D30T_AG and the one line_X180Y780_120D30T_AU, dependent properties of the thickness G of the light-transmissive layer of the wavelength exhibiting the minimum value of the reflectance spectrum are studied. FIGS. 16A-D are graphs in which the wavelength of the minimum value in the reflectance spectrum is plotted with respect to the thickness G of the light-transmissive layer. In FIGS. 16A-D, in addition to a main minimum peak (a black square (a filled square)), a sub minimum peak (a black rhombus (a black diamond) (a filled rhombus; a filled diamond)) is plotted, the sub minimum peak occurs due to an interference resonance effect which occurs in the light-transmissive layer, and anti-crossing behavior does not occur.

From FIGS. 16A-D, a minimum value of a value of the minimum peak of the reflectance due to the interference resonance effect is observed when the metallic particles are AG and the thickness G of the light-transmissive layer is in the vicinity of 220 nm and when the metallic particles are AU and the thickness G of the light-transmissive layer is in the vicinity of 260 nm, and when the thickness G is smaller than the above-described range, the value of the smallest value of the reflectance increases.

For this reason, each reflectance spectrum (far-field properties) is acquired when the metallic particles are AG and the thickness G of the light-transmissive layer is 220 nm and when the metallic particles are AU and the thickness G of the light-transmissive layer is 260 nm. A result thereof is shown in FIGS. 17A and B. FIGS. 17A and B illustrate far-field properties of models of X180Y780_AG_220G_120-140D and X180Y780_AU_260G_110-130D in the thickness G of the light-transmissive layer in which an interference resonance occurs.

From FIGS. 17A and B, the interference resonance effect is a peak on a short wavelength side, a half-value width FWHM of 220G is 26 nm in Ag, and a half-value width FWHM of 260G is 46 nm in Au. Whereas, in the model of one line_X180Y780_130DAG in FIG. 15, it is found that FWHM is greater than or equal to 60 nm in a range of 20G to 140G, and thus when comparing this, the peak which occurs due to the interference resonance in the reflectance spectrum has a narrow half-value width, it is difficult to increase the enhancement degree in a wide wavelength bandwidth, and as a Raman sensor, designing the electric field enhancing element by using this effect is not necessarily optimum. For example, when FWHM of Ag is 26 nm, only a Raman shift of 0 cm$^{-1}$ to 400 cm$^{-1}$ is able to be measured, and thus it is not suitable for the Raman sensor. For example, a device disclosed in JP-A-2009-115492 uses an interference resonance, is a method in which a change in a dielectric constant due to attachment of a sensing substance is detected by narrowing a half-value width, that is, a method in which a shift amount of a peak wavelength or a change in reflectance of a fixed wavelength in the vicinity of the peak wavelength is detected, and is different from a method described herein in which a high enhancement degree is able to be obtained in a wide wavelength bandwidth by increasing the half-value width.

4.2. Experimental Example 2

Near-Field Properties of One Line⊥Model

Figure 16B:
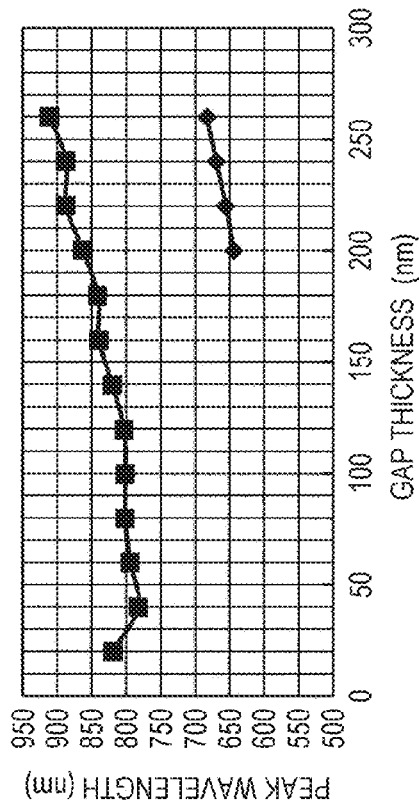
FIGS. 16A-D are graphs illustrating dependent properties of a wavelength having a peak in a reflectance spectrum and a minimum value of the peak in the reflectance spectrum in the model according to the experimental example with respect to a thickness of a light-transmissive layer.
Figure 16D:
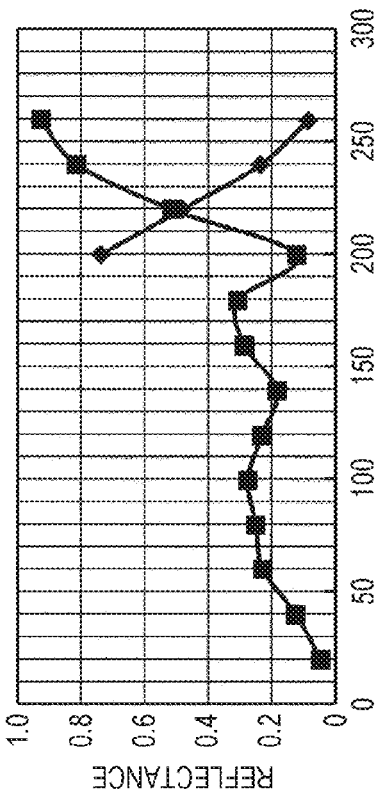
Figure 16A:
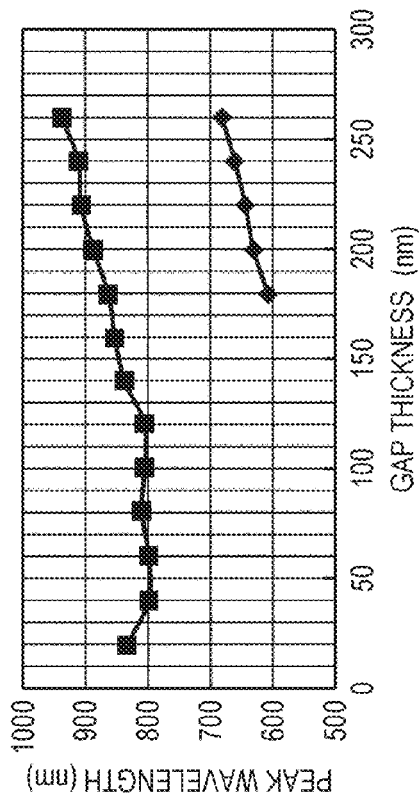
Figure 16C:
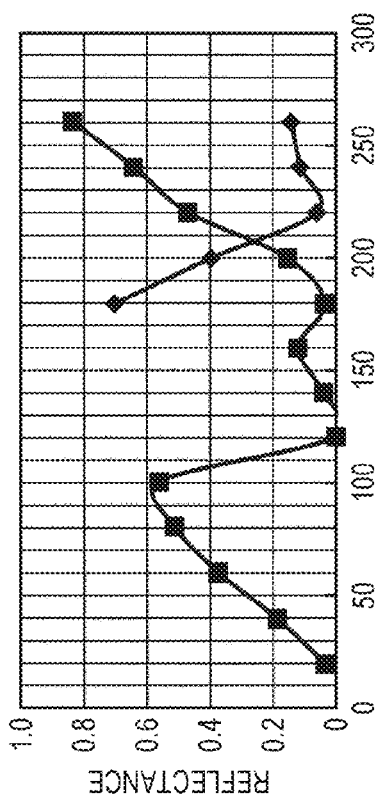
Figure 18B:
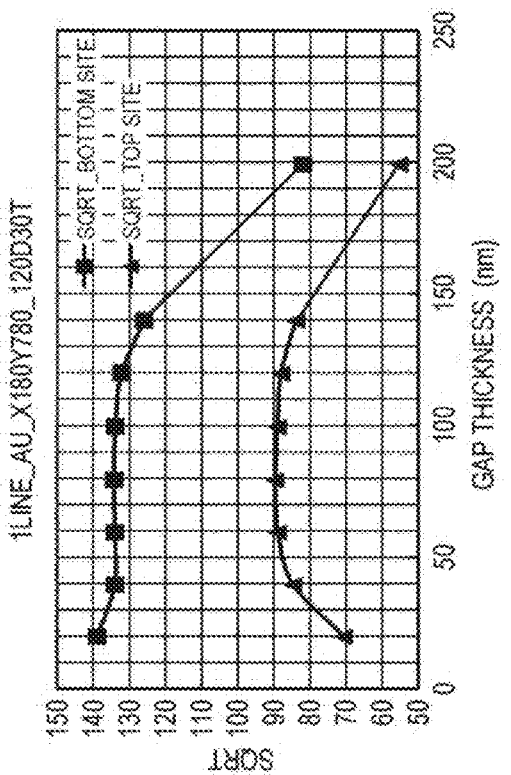
FIGS. 18A-D are graphs illustrating light-transmissive layer thickness dependent properties of SQRT and a top/bottom ratio of the model according to the experimental example.
Figure 18D:
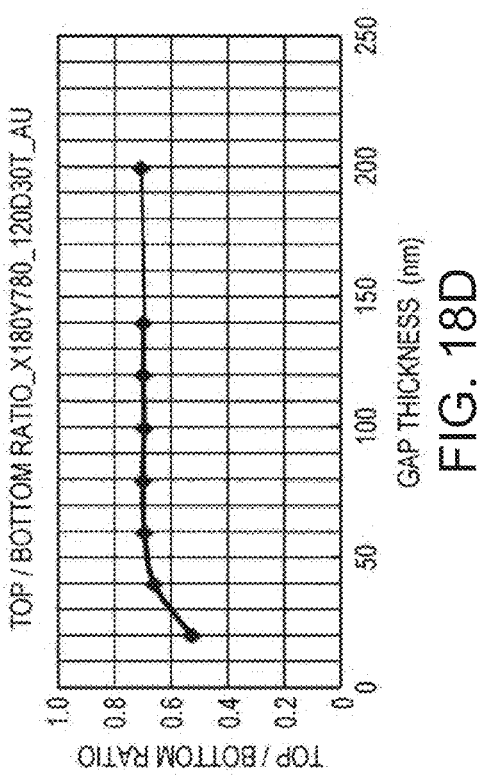
Figure 18A:
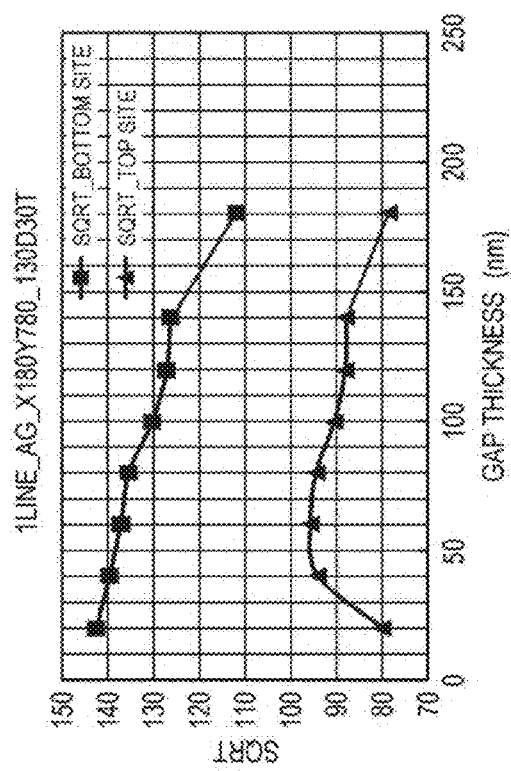
Figure 18C:
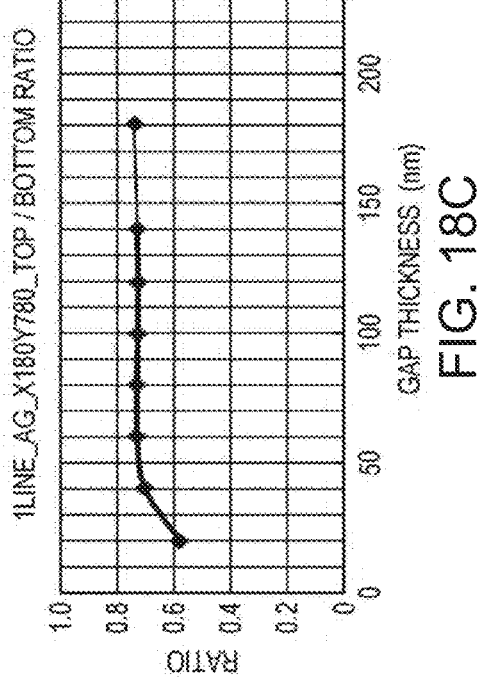

With reference to reflectance properties in a far-field illustrated in FIGS. 16C and D, when the thickness G of the light-transmissive layer increases, the minimum value of the reflectance gradually rises. It is considered that this is because the far-field properties cause an integration value in a hot spot of a lower portion (the bottom) or an upper portion (the top) of the metallic particles. In this experimental example, dependent properties of the thickness G of the light-transmissive layer in each hot spot are inquired, and thus the near-field properties of this model are acquired. A result thereof is shown in FIGS. 18A-D.

The bottom indicates an enhancement degree of a surface boundary between the metallic particles and SiO$_2$ (the light-transmissive layer), the top indicates an enhancement degree of an upper surface of the metallic particles, and a (top/bottom) ratio indicates a value of a rate of SQRT in each position. As obvious from FIGS. 16A-D described above, a wavelength exhibiting a peak of an enhancement degree is changed according to the thickness G of the light-transmissive layer, and thus SQRT of FIGS. 18A and B is a graph in which an enhancement degree (SQRT) in a wavelength exhibiting the greatest enhancement degree (the smallest reflectance) is obtained and plotted.

FIGS. 18A-D are plots with respect to the thickness G of the light-transmissive layer of SQRT of a one line⊥_X180Y780_130D30T_AG model and a one line⊥_X180Y780_120D30T_AU model, and a plot with respect to the thickness G of the (top/bottom) ratio of this model.

From FIGS. 18A-D, when the material of the metallic particles are Ag or Au, SQRT of the bottom gradually decreases as a value of G considerably increases from 20 nm, and SQRT of the top is the greatest value when the metallic particles are Ag and G is approximately 60 nm and when the metallic particles are Au and G is approximately 80 nm.

That is, it is able to be understood that the electric field enhancing (SQRT) of the bottom is a mode based on LSP generated in the thickness direction of the light-transmissive layer, and the electric field enhancing of the top is a mode based on PSP generated in the metallic layer. In the model of FIGS. 18A-D, LSP in which LSP generated in the metallic interparticle in the X direction (a direction in parallel with the flat surface of the light-transmissive layer) and LSP generated in the thickness direction of the light-transmissive layer are combined is consistently coincident with a mechanism indicating a high enhancement degree due to the mutual interaction between LSP and PSP of the Y direction generated in the metallic layer.

As described above, a target substance in a sample is easily attached to a position of the top of the metallic particles. In the model of FIGS. 18A-D, the thickness G of the light-transmissive layer indicating SQRT which is greater than or equal to SQRT when the thickness G of the light-transmissive layer is 20 nm is able to be greater than or equal to 20 nm and less than or equal to 170 nm. In addition, from FIGS. 18A-D, it is found that the (top/bottom) ratio is a constant value from the vicinity of a portion in which the thickness G of the light-transmissive layer exceeds 40 nm to 50 nm. That is, when the thickness G of the light-transmissive layer is greater than or equal to 40 nm, it is difficult for the (top/bottom) ratio to be changed even when G varies, and for example, it is possible to increase an allowable range of a variation in a film thickness of the light-transmissive layer in manufacturing. In addition, when the thickness G of the light-transmissive layer is greater than or equal to 40 nm, the (top/bottom) ratio increases compared to a case where the thickness G is less than 40 nm, and thus energy granted by the excitation light is able to be more greatly distributed to the top side, and it is possible to more efficiently measure the target substance.

Next, a case where a wavelength of the excitation light is different is inquired. FIGS. 19A-D are plots with respect to the thickness G of the light-transmissive layer of SQRT of a one line⊥_X180Y600_100D30T_AG model and a one line⊥X180Y780_130D30T_AG model, and a plot with respect to the thickness G of a (top/bottom) ratio of this model. A mesh used for calculation is XY1nmZ1-5nmGG. In addition, similar to a case of FIGS. 18A-D described above, a wavelength exhibiting a peak of an enhancement degree is changed according to the thickness G of the light-transmissive layer, and thus in SQRT of FIGS. 19A and B, an enhancement degree (SQRT) in a wavelength exhibiting the greatest enhancement degree (the smallest reflectance) is obtained and plotted.

From FIGS. 19A-D, in a case of Y600 (FIGS. 19A and C), SQRT of the bottom gradually decreases with a small maximum as a value of G increases from 20 nm, and in a case of Y780 (FIGS. 19B and D), SQRT of the bottom gradually and monotonously decreases as the value of G increases from 20 nm. On the other hand, SQRT of the top is the greatest value when G is approximately 40 nm to 100 nm in Y600 and when G is approximately 60 nm in Y780.

In the model of FIGS. 19A-D, the thickness G of the light-transmissive layer indicating SQRT which is greater than or equal to SQRT when the thickness G of the light-transmissive layer is 20 nm is able to be greater than or equal to 20 nm and less than or equal to 140 nm in Y600 (an excitation model of 633 nm). In addition, in Y780 (an excitation model of 785 nm), the thickness G of the light-transmissive layer indicating SQRT which is greater than or equal to SQRT when the thickness G of the light-transmissive layer is 20 nm is able to be greater than or equal to 20 nm and less than or equal to 175 nm.

Further, from the graph in FIGS. 19A-D, it is found that the (top/bottom) ratio is approximately a constant value from the vicinity of a portion in which the thickness G of the light-transmissive layer exceeds 40 nm to 50 nm. That is, when the thickness G of the light-transmissive layer is greater than or equal to 40 nm, it is difficult for the (top/bottom) ratio to be changed even when G varies, and for example, it is possible to increase an allowable range of a variation in a film thickness of the light-transmissive layer in manufacturing. In addition, when the thickness G of the light-transmissive layer is greater than or equal to 40 nm, the (top/bottom) ratio increases compared to a case where the thickness G is less than 40 nm, and thus energy granted by the excitation light is able to be more greatly distributed to the top side, and it is possible to more efficiently measure the target substance.

Further, it is considered that an upper limit value of the thickness G of the light-transmissive layer indicating SQRT which is greater than or equal to SQRT when the thickness G of the light-transmissive layer is 20 nm is proportionate to the wavelength of the excitation light, the upper limit value is able to be standardized by using both values, and in this case, a proportional constant number (a correction term) is able to be (633 nm/785 nm).

From a result of FIGS. 19A-D, a relationship between the excitation model of 633 nm and the excitation model of 785 nm is able to be known. That is, in the excitation model (Y600) of 633 nm, the upper limit value of the thickness G of the light-transmissive layer indicating SQRT which is greater than or equal to SQRT when the thickness G of the light-transmissive layer is 20 nm is 140 nm, and in the excitation model (Y780) of 785 nm, the upper limit value of the thickness G of the light-transmissive layer indicating SQRT which is greater than or equal to SQRT when the thickness G of the light-transmissive layer is 20 nm is 175 nm.

Then, it is confirmed that when the upper limit value of 175 nm of the thickness G of the light-transmissive layer in the excitation model of 785 nm is multiplied by (633 nm/785 nm), a result thereof is 141 nm, and thus the result is approximately coincident with the upper limit value of 140 nm of the thickness G of the light-transmissive layer in the excitation model (Y600) of 633 nm.

4.3. Experimental Example 3

Far-Field Properties of One Line//Model

Figure 20A:
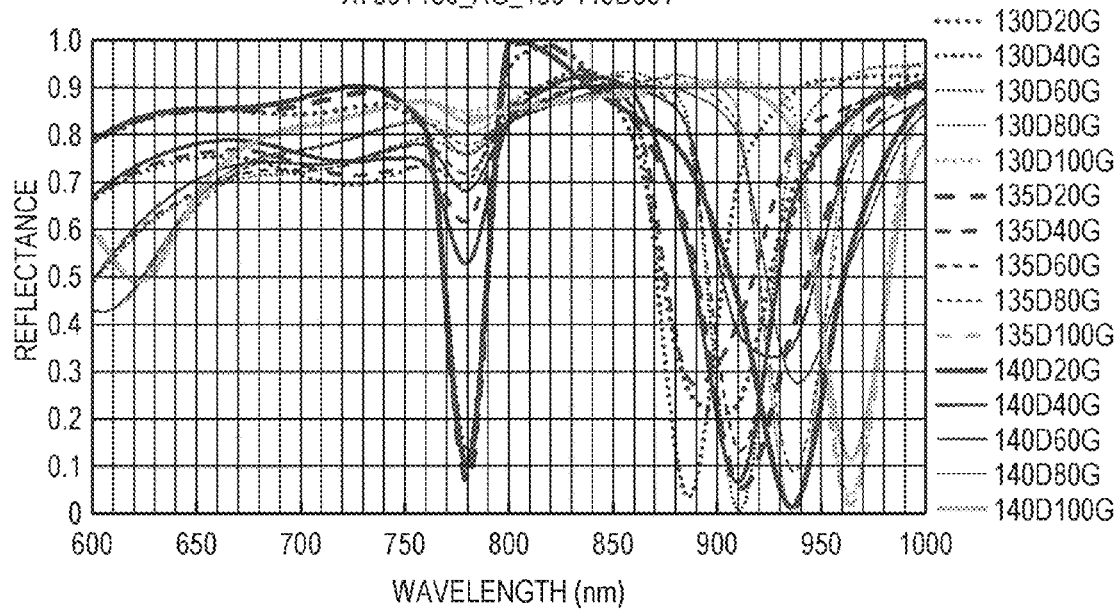
FIGS. 20A and B are reflectance spectrums of the model according to the experimental example.
Figure 20B:
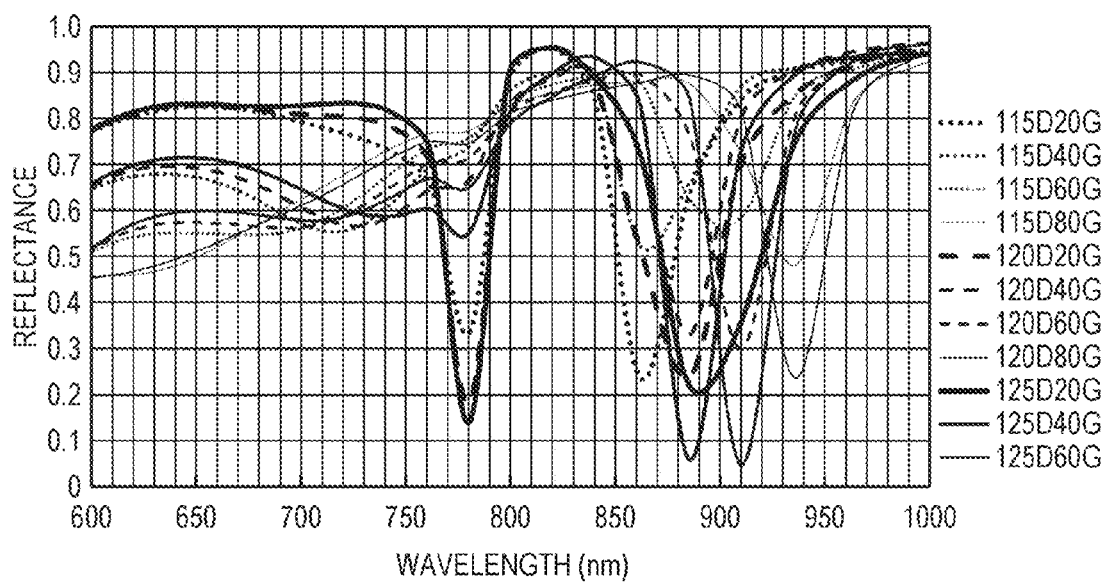
Figures 21A, 21B:
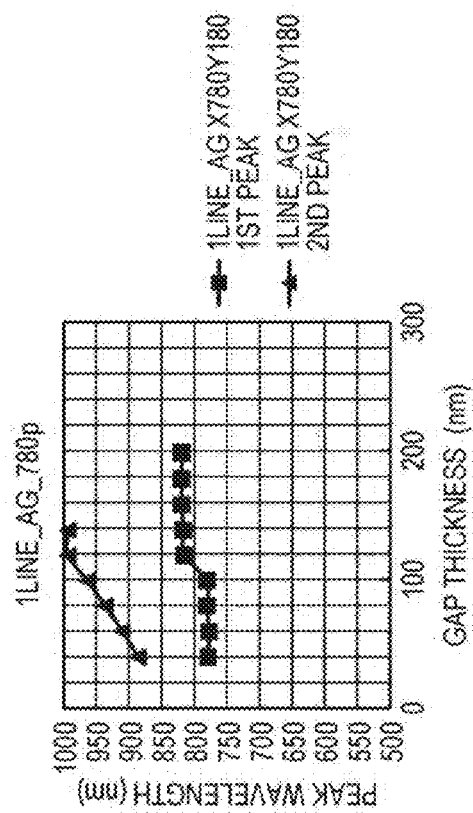
FIGS. 21A-D are graphs illustrating the dependent properties of the wavelength having a peak in the reflectance spectrum and the minimum value of the peak in the reflectance spectrum in the model according to the experimental example with respect to the thickness of the light-transmissive layer.
Figures 21C, 21D:
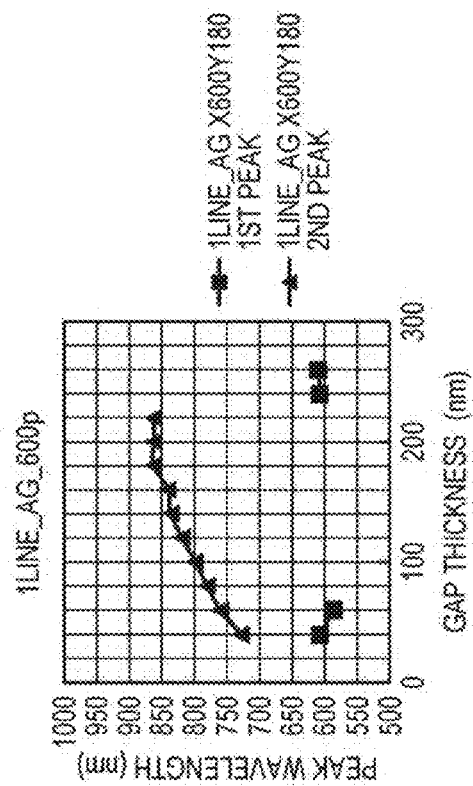

Next, a reflectance spectrum of a model of one line// X780Y180 is illustrated in FIGS. 20A and B. A polarization direction of the excitation light is the X direction, and is a mode in which hybrid between PSP and LSP occurs in the X direction. In this case, anti-crossing behavior occurs, and thus a peak indicating two smallest values appears in a reflectance spectrum.

In FIGS. 20A and B, a reflectance spectrum of one line//_X780Y180_130-140D30T_AG_20-100G and one line//_X780Y180_115-125D30T_AU_20-80G is illustrated.

It is found that when the thickness G of the light-transmissive layer is 20 nm, a peak wavelength having a peak observed in the vicinity of 780 nm (a downwardly protruding peak in a graph having the smallest value) is constant without depending on a diameter D of the metallic particles when the material of the metallic particles is Ag or Au, and a peak wavelength having a peak on a long wavelength side (a peak observed in a range of 0.85 μm to 1 μm) is shifted by approximately 30 nm by changing the diameter by 10 nm when the material of the metallic particles is Ag or Au.

In contrast, it is found that when the thickness G of the light-transmissive layer is 60 nm, in a peak in the vicinity of a short wavelength of 780 nm, the smallest value of reflectance increases (the peak decreases), but the peak wavelength is constantly 780 nm without depending on the diameter D when the material of the metallic particles is Ag or Au. Then, it is found that a peak on a long wavelength side is shifted to approximately 10 nm by changing the diameter by 10 nm when the material of the metallic particles is Ag or Au.

FIGS. 21A-D are graphs in which a wavelength of the smallest peak obtained from the far-field properties illustrated in FIGS. 20A and B is plotted for each model. From FIGS. 21A-D, in the one line//model, it is found that even when the thickness G of the light-transmissive layer ($SiO_2$) is changed in a range of 40 nm to 140 nm in any model, a wavelength having a peak on the short wavelength side is rarely changed ("a black square (a filled square)" in the graph). Whereas, it is found that a wavelength having a peak on the long wavelength side is monotonously shifted to the long wavelength side as the thickness G of the light-transmissive layer ($SiO_2$) increases from 40 nm ("a black triangle (a filled triangle)" in the graph).

It is considered that a phenomenon in which the peak wavelength having a peak on the long wavelength side is shifted to the long wavelength side according to an increase in G occurs because an effective refractive index in the vicinity of the metallic layer of gold (Au) increases in proportion to the increase in G and a dispersion relationship of the transmissive plasmon (PSP) generated in the metallic layer is shifted to the long wavelength side.

4.4. Example 4

Near-Field Properties of One Line//Model

Similar to Experimental Example 2, in an enhancement degree (SQRT) of a position of the top of the metallic particles of a model of one line//X780Y180, dependent properties with respect to the thickness G of the light-transmissive layer are inquired. A wavelength exhibiting a peak of an enhancement degree is changed according to the thickness G of the light-transmissive layer, and thus as SQRT, an enhancement degree (SQRT) in each wavelength of 620 nm, 630 nm, and 640 nm is used.

Figure 22:
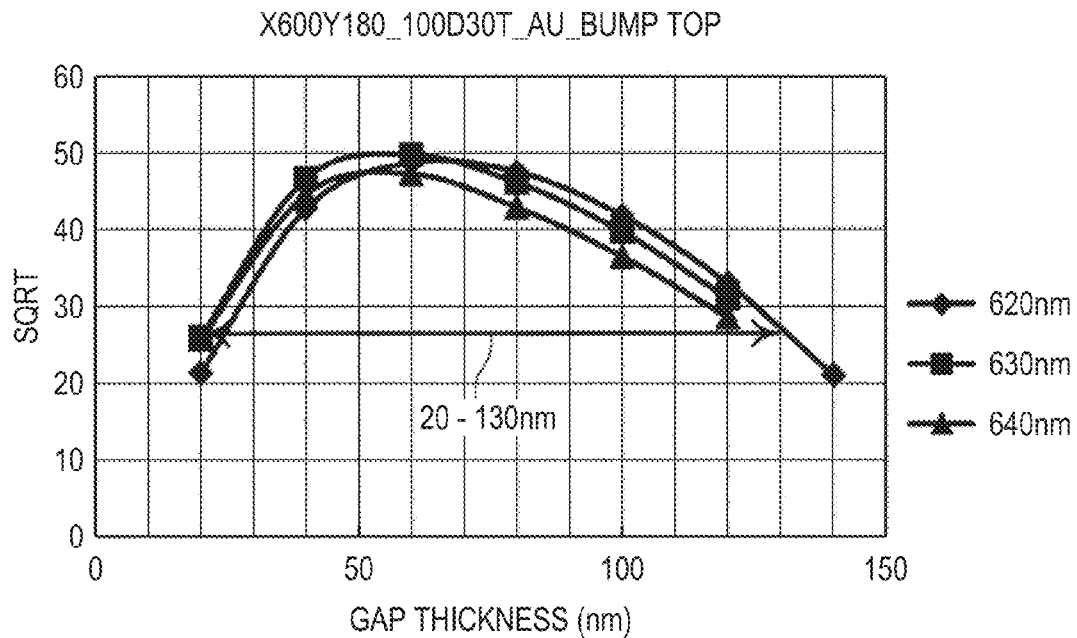
FIG. 22 is a graph illustrating the light-transmissive layer thickness dependent properties of SQRT of the model according to the experimental example.

FIG. 22 is a graph in which SQRT of the top of the metallic particles of a model of one line//_X600Y180_100D30T_AU is plotted with respect to the thickness G of the light-transmissive layer.

With reference to FIG. 22, it is found that when the thickness G of the light-transmissive layer is 20 nm, a value of SQRT increases when excitation occurs in a wavelength of 630 nm and 640 nm. Then, a range of the thickness G of the light-transmissive layer indicating a value of SQRT greater than this value is greater than or equal to 20 nm and less than or equal to 130 nm without depending on the wavelength of the excitation light.

From this result, the following is found. In the near-field properties of the one line//model, it is found that when the thickness G of the light-transmissive layer is 20 nm, a (top/bottom) ratio decreases without depending on a dimension of the model, that is, plasmon generated in the bottom of the metallic particles is relatively strong. It is considered that this is because when the thickness G of the light-transmissive layer is approximately 20 nm, the enhancement degree is dominant by LSP in the thickness direction of the light-transmissive layer. In addition, it is found that when the thickness G of the light-transmissive layer is approximately 20 nm, a wavelength having a peak indicating minimum reflectance is greatly changed according to a variation in the diameter D of the metallic particles, and thus for example, high dimensional accuracy is required at the time of manufacturing. Further, it is considered that when the thickness G of the light-transmissive layer is approximately 20 nm, an enhancement degree in a top end of the metallic particles to which the target substance is easily attached is relatively small, and thus usage efficiency of energy decreases. For this reason, in the excitation model of 633 nm of one line//, it is found that the thickness G of the light-transmissive layer is greater than 20 nm and less than or equal to 130 nm, and thus the electric field enhancing element has a high overall electric field enhancing effect.

4.5. Experimental Example 5

Generalization of Numerical Value Range

Correction Term

As obtained in each experimental example described above, a preferred range of the thickness G of the light-transmissive layer such as 20 nm<G≤160 nm is a range derived from a case where the wavelength of the excitation light in the vertical incidence is 785 nm and the material of the light-transmissive layer is $SiO_2$ having n of 1.46. In addition, from FIGS. 19A-D and FIG. 22, in the excitation model of 785 nm (X180Y780) and the excitation model of 633 nm (X180Y600), a range of G indicating SQRT exceeding SQRT when G is 20 nm is 20 nm<G≤140 nm in the excitation model of 633 nm, and is 20 nm<G≤175 nm in the excitation model of 785 nm of one line⊥model.

In addition, in the one line//model, the range is 20 nm<G≤130 nm in the excitation model of 633 nm.

For this reason, in the excitation model of 785 nm, an upper limit value of G is derived from 130 nm·(785 nm/633 nm)=161 nm, and thus when an upper limit of this expression is 160 nm, 20 nm<G≤160 nm·(wavelength of excitation light nm)/785 nm is derived.

In addition, a preferred thickness G of the light-transmissive layer in the model described above is in a range when the material of the light-transmissive layer is $SiO_2$, and the range described above is shifted with respect to the refractive index of the light-transmissive layer. Specifically, in the range of 20 nm<G≤160 nm when the material of the light-transmissive layer is $SiO_2$, a light-transmissive layer of other materials is able to be standardized. That is, by using $SiO_2$ having a refractive index of 1.46, 20 nm<G·(refractive index of light-transmissive layer/1.46)≤160 nm is able to be expressed. For example, it is found that when the material of the light-transmissive layer is $TiO_2$, the refractive index of the light-transmissive layer is 2.49, and the range is 11 nm<G≤94 nm.

In addition, the light-transmissive layer may be formed of a multi-layer, and similarly, in this case, a preferred range is able to be determined by using an effective refractive index. For example, when the light-transmissive layer has a laminated structure of an $Al_2O_3$ layer having a thickness of 10 nm (a refractive index of 1.64) and a $SiO_2$ layer having a thickness of 30 nm (a refractive index of 1.46), (1.64·10 nm+1.46·30 nm)/1.46=41.2 nm is satisfied, and thus it is able to be considered to be identical to a case where the light-transmissive layer is a $SiO_2$ layer having a thickness of 41.2 nm.

4.6. Experimental Example 6

Design of Enhancement Degree Profile

As illustrated in FIGS. 16A-D, in the one line⊥model in which the mutual interaction between LSP and PSP is strong, when the thickness G of the light-transmissive layer is greater than or equal to 40 nm and less than or equal to 160 nm, a change in the peak wavelength is small, and one broad peak appears, and thus the thickness G of the light-transmissive layer is able to be designed such that a high enhancement degree is obtained with respect to the target substance having a small Raman shift amount.

In this case, a half-value width (FWHM) is slightly different according to the model, but as illustrated in FIG. 15, FWHM is comparatively large as greater than or equal to 60 nm, and in the excitation model of 633 nm, a Raman shift corresponding to a wavelength up to 693 nm, that is, a Raman shift up to 1350 $cm^{-1}$ in a wavenumber is able to be covered. On the other hand, in the excitation model of 785 nm, a Raman shift corresponding to a wavelength up to 845 nm, that is, a Raman shift up to 900 $cm^{-1}$ in a wavenumber is able to be covered.

Figure 23:
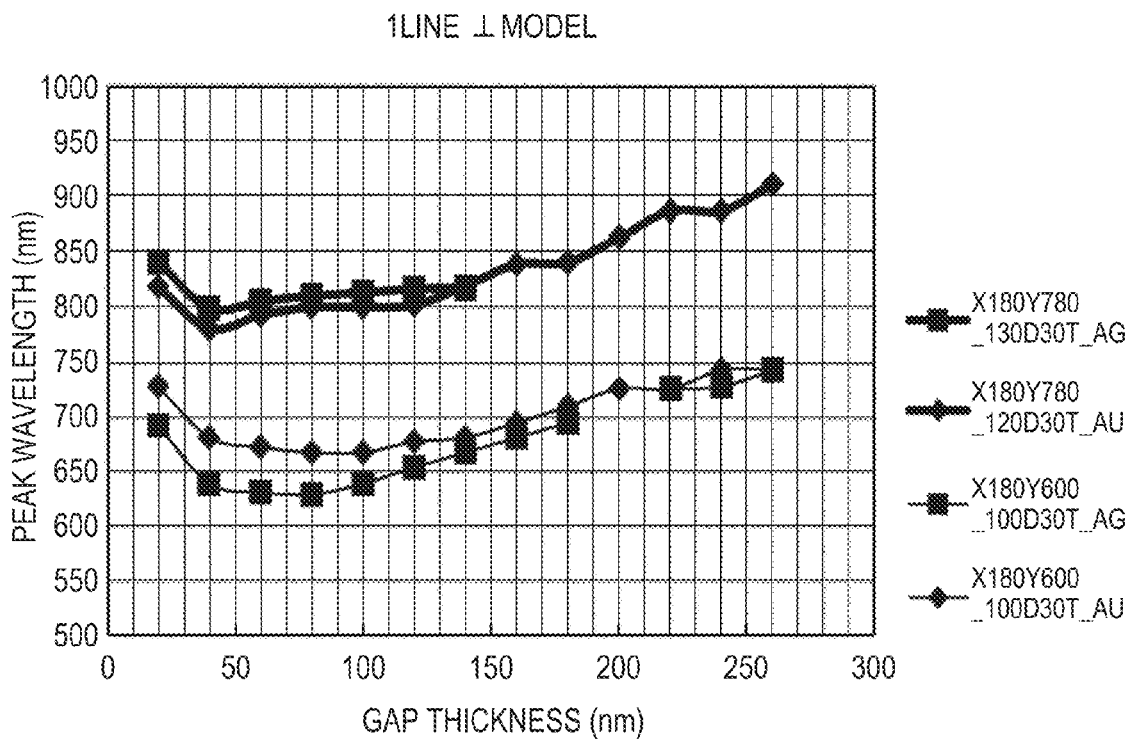
FIG. 23 is a graph illustrating light-transmissive layer thickness dependent properties of a minimum wavelength having a peak in the reflectance spectrum of the model according to the experimental example.

In FIG. 23, dependent properties of the thickness G of the light-transmissive layer having a wavelength with a peak in a reflectance spectrum of the one line⊥model are illustrated. On the other hand, in the one line//model, as illustrated in FIGS. 21A-D, it is found that when the light-transmissive layer is $SiO_2$ regardless of a dimension of the model, the peak wavelength having a peak on the short wavelength side is rarely changed with respect to the thickness G of the light-transmissive layer, and when the thickness G of the light-transmissive layer increases, the peak on the long wavelength side is shifted to the long wavelength side.

It is considered that the wavelength having a peak on the long wavelength side is shifted to the long wavelength side along with an increase in the thickness G of the light-transmissive layer because the effective refractive index in the vicinity of the metallic layer increases in proportion to a thickness of a gap, and a dispersion relationship of the transmissive plasmon (PSP) of the metallic layer is shifted to the long wavelength side.

In the excitation model of 633 nm, the peak on the long wavelength side is able to cover a wavelength greater than or equal to 710 nm, that is, a wavenumber greater than or equal to 1750 cm$^{-1}$, and a wavelength less than or equal to 853 nm, that is, a wavenumber less than or equal to 4100 cm$^{-1}$. In addition, in the excitation model of 785 nm, the peak on the long wavelength side is able to cover a wavelength greater than or equal to 880 nm, that is, a wavenumber greater than or equal to 1400 cm$^{-1}$, and a wavelength less than or equal to 976 nm, that is, a wavenumber less than or equal to 2500 cm$^{-1}$.

FIG. 24A is a case where the polarization direction is the X direction (a P1 direction) in an X180Y780_130D30T_60G_AG model (⊥model), and FIG. 24B is a case where the polarization direction is the Y direction (a P2 direction) (//model). It is found that Raman scattering light of 787 cm$^{-1}$ (excitation of 785 nm, and scattering of 837 nm) of acetone is able to be detected in ⊥model, and Raman scattering light of 1708 cm$^{-1}$ (excitation of 785 nm, and scattering of 907 nm) of acetone is able to be detected in //model. In FIGS. 25A-D, generalization thereof is illustrated, a Raman scattering wavelength is derived by a Raman shift amount to be sensed as an excitation wavelength, and from FIGS. 25A-D, the Raman scattering wavelength may be the thickness of the light-transmissive layer having an enhancing peak in this Raman scattering wavelength. The following summarizes the above descriptions.

1. Case of Excitation of 633 nm

In order to increase the enhancement degree in a wide wavelength bandwidth, it is effective that the thickness of the light-transmissive layer corresponds with a value of the Raman shift by using the one line⊥model when the Raman shift of the target substance is 0 cm$^{-1}$ to 1350 cm$^{-1}$ (692 nm), and by using the one line//model when the Raman shift is 1750 cm$^{-1}$ (712 nm) to 4100 cm$^{-1}$ (853 nm).

2. Case of Excitation of 785 nm

In order to increase the enhancement degree in a wide wavelength bandwidth, it is effective that the thickness of the light-transmissive layer corresponds with a value of the Raman shift by using the one line⊥model when the Raman shift of the target substance is 0 cm$^{-1}$ to 900 cm$^{-1}$ (845 nm), and by using the one line//model when the Raman shift is 1400 cm$^{-1}$ (880 nm) to 2500 cm$^{-1}$ (976 nm).

Then, when the Raman scattering light from the target substance having the Raman shift of 1350 cm$^{-1}$ (692 nm) to 1750 cm$^{-1}$ (712 nm) in the case of (1) and the Raman shift of 900 cm$^{-1}$ (845 nm) to 1400 cm$^{-1}$ (880 nm) in the case of (2) is enhanced, it is possible to broaden the reflectance spectrum compared to the one line⊥model and it is possible to enhance the scattering light of the wavenumber range described above by increasing density of arranging the metallic particles (for example, by narrowing the pitch in the Y direction by using X180Y400 instead of X180Y600 or the like) or by setting the number of rows of the metallic particle row to be a plurality of rows (to be a multi-line).

When a case where the target substance is acetone is described as an example in detail, first, it is found that the Raman shift of 787 cm$^{-1}$, 1708 cm$^{-1}$, and 2921 cm$^{-1}$ is generated in acetone. Then, when the excitation wavelength $\lambda_i$ is 633 nm, each wavelength $\lambda_s$ after the stokes Raman scattering is 666 nm, 709 nm, and 777 nm corresponding to the Raman shift. In addition, when the excitation wavelength $X_i$ is 785 nm, each wavelength $X_s$ after the stokes Raman scattering is 837 nm, 907 nm, and 1019 nm corresponding to the Raman shift.

FIGS. 24A and B are diagrams for illustrating a relationship between the wavelength characteristic of the reflectance (the enhancement degree) and the excitation wavelength and the scattering wavelength of SERS. For example, as illustrated in FIGS. 24A and B, in order to detect the Raman scattering light of 787 cm$^{-1}$ of acetone, the excitation wavelength $\lambda_i$ is 785 nm, and each wavelength $\lambda_s$ after the stokes Raman scattering is 837 nm, and thus when one line_X180Y780_130D30T_60G_AG in which the polarization direction is the X direction is used, it is possible to enhance the Raman scattering light of 787 cm$^{-1}$ of acetone to be strong, and it is possible to obtain a strong SERS signal.

In addition, in order to enhance the Raman scattering light of 1708 cm$^{-1}$ of acetone to be strong, when the excitation wavelength $\lambda_i$ is 785 nm, the wavelength $\lambda_s$ after the stokes Raman scattering is 907 nm, and thus when one line_X780Y180_130D30T_AG_60G in which the polarization direction is the X direction is used, it is possible to enhance the Raman scattering light of 1708 cm$^{-1}$ of acetone to be strong, and it is possible to obtain a strong SERS signal.

Furthermore, a one line_X780Y180_130D30T_AG_60G model in which the polarization direction is the X direction is entirely identical to a one line_X180Y780_130D30T_AG_60G model in which the polarization direction is the Y direction. For this reason, in the above-described example, in order to enhance each Raman scattering light, it is understood that it is not necessary to prepare two electric field enhancing elements, and it is possible to enhance the Raman scattering light having a Raman shift in a wide range according to one electric field enhancing element only by changing the polarization direction of the excitation light into the X direction and the Y direction. In addition, when circularly polarized light is used, it is possible to simultaneously acquire the SERS signals acquired by using the linearly polarized light in the X direction and the linearly polarized light in the Y direction.

In FIGS. 25A-D, dependent properties of the thickness G of the light-transmissive layer of a peak wavelength of (one line//model) having two peaks obtained in FIGS. 21A-D, and dependent properties of the thickness G of the light-transmissive layer of a peak wavelength of (one line⊥model) having one peak obtained in FIG. 23 are illustrated.

It is understood that the one line⊥model and the one line//model are physically (structurally) the same electric field enhancing element, and have a degree of freedom such that a wavelength region in which a high enhancement degree is obtained is able to be selected according to a difference in the polarization direction of the excitation light between the X direction and the Y direction, and a high SERS signal is able to be acquired according to the target substance.

4.7. Experimental Example 7

Experimental Examples 1 to 6 described above are calculated by setting the metallic layer as being entirely formed of gold (Au). In contrast, each experiment when the material of the metallic layer is silver (Ag) is performed, but there is no great difference between these experiments. In addition, as the material of the light-transmissive layer, $Al_2O_3$, $TiO_2$, and the like are able to be used in addition to $SiO_2$. When a material other than $SiO_2$ is used for the light-transmissive layer, the thickness G of the light-transmissive layer may be set in consideration of a refractive index of the material other than $SiO_2$ by using $SiO_2$ of Experimental Examples 1 to 6 as a base. For example, in a case where it is preferable that the thickness of the light-transmissive layer when the material is $SiO_2$ is in a range greater than 20 nm and less than or equal to 160 nm, when the material of the light-transmissive layer is TiO$_2$, a preferred thickness G of the light-transmissive layer is able to be obtained by multiplying the thickness of the light-transmissive layer when the material is SiO$_2$ by a value of (1.46/2.49) in consideration of a refractive index (2.49) of TiO$_2$. Therefore, when the material of the light-transmissive layer is TiO$_2$, the preferred thickness G of the light-transmissive layer is approximately greater than 12 nm and less than or equal to 94 nm.

In addition, in Experimental Examples 1 to 6 described above, a model in which the metallic particles are arranged at a pitch of 600 nm is used as the excitation model of 633 nm, and a model in which the metallic particles are arranged at a pitch of 780 nm are used as the excitation model of 785 nm, but the model is not limited thereto.

Figure 26:
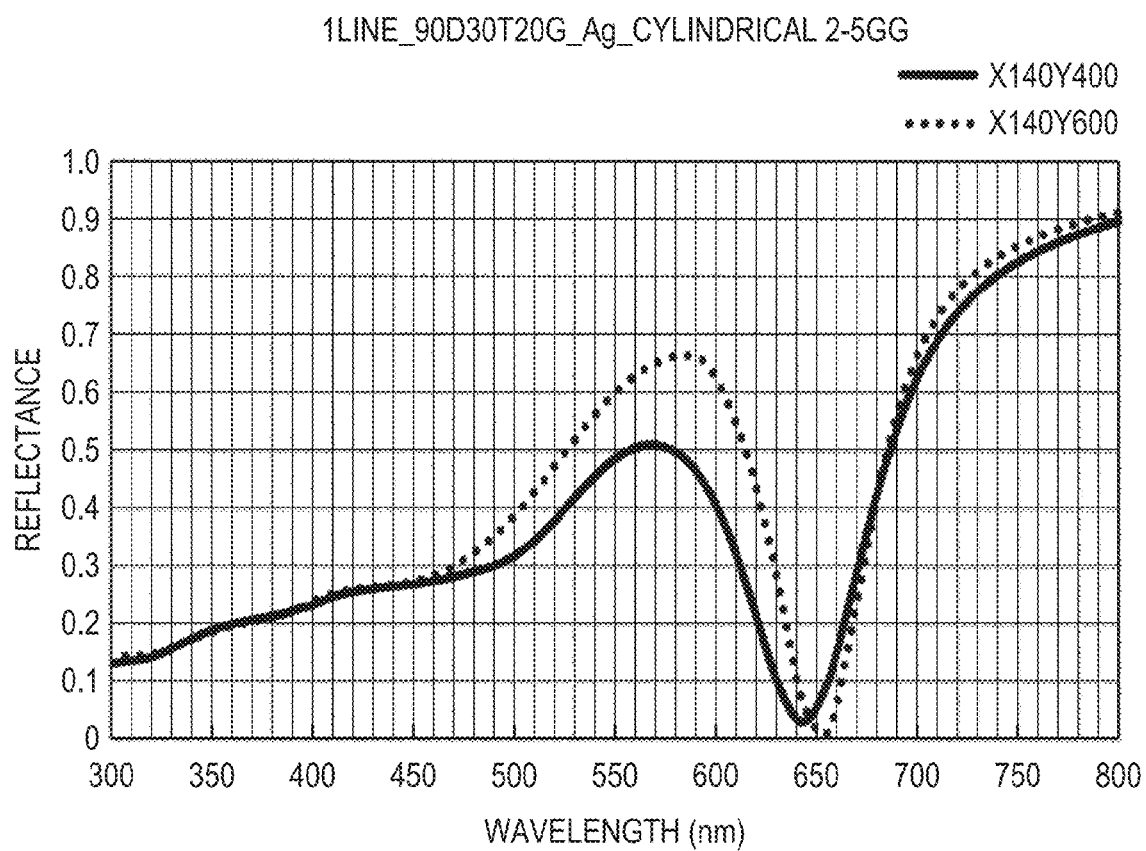
FIG. 26 is the reflectance spectrum of the model according to the experimental example.

In addition, as an example in which density of arranging the metallic particles is increased by narrowing the pitch in the Y direction of the one line⊥model of the excitation of 633 nm, a graph illustrating a comparison between reflectance spectrums of a one line ⊥_X140Y600_90D30T model and a one line ⊥_X140Y400_90D30T model is illustrated in FIG. 26.

As illustrated in FIG. 26, it is understood that even when the density of arranging the metallic particles is increased as the one line ⊥_X140Y400_90D30T model, behavior identical to that of the one line ⊥_X140Y600_90D30T model is shown. Furthermore, it is considered that when comparing details, an enhancement degree of a peak (the smallest value of reflectance) is smaller in the one line ⊥_X140Y400_90D30T model than in the one line ⊥_X140Y600_90D30T model, but a half-value width is wide, and thus a more preferred electric field enhancing element is obtained according to the target substance. Further, signal intensity of SERS is proportionate to hot spot density, and thus intensity of the SERS signal increases by an increase in the hot spot density (HSD) by increasing the density of arranging the metallic particles.

In addition, in all of the experimental examples described above, the shape of the metallic particles is a cylinder, but may be an ellipse or a prism. When the shape of the metallic particles is a prism, it is possible to further increase the enhancement degree. Further, as the wavelength of the excitation light, HeNe laser of 633 nm and semiconductor laser of 785 nm are considered, but the wavelength is not limited thereto. Even when the wavelength of the excitation light is different from this wavelength, as described above, the thickness G of the light-transmissive layer is able to be determined according to the wavelength. Further, as the size of the metallic particles, a diameter of 80 nm to 160 nm and a thickness of 30 nm are calculated, but the size is not limited thereto. Furthermore, when the diameter decreases and the thickness decreases or when the diameter increases and the thickness increases, it is possible to obtain a wavelength characteristic identical to or similar to that of each experimental example. For example, even when the size is small as 34D4T, the wavelength characteristic as described above is obtained.

5. Other Matters

FIGS. 27A-D are schematic views illustrating a relationship between the arrangement of the metallic particles and LSP (Localized Surface Plasmon Resonance (LSPR)) and PSP (Propagating Surface Plasmon Resonance (PSPR)). Herein, for the convenience of the description, a case where LSP is simply generated in the vicinity of the metallic particles has been described. The electric field enhancing element has anisotropy in the arrangement of the metallic particles (P1<P2), and thus SPR used in the electric field enhancing element is generated by electromagnetically and mutually interacting LSP with PSP.

Here, it is found that in LSP which is able to be generated in the vicinity of the metallic particles, two modes of a mode in which LSP is generated between the adjacent metallic particles (hereinafter, referred to as "Particle-Particle Gap Mode (PPGM)"), and a mode in which LSP is generated between the metallic particles and the metallic layer (having a function of a mirror) (hereinafter, referred to as "Particle-Mirror Gap Mode (PMGM)") exist (refer to FIGS. 27A-D).

The excitation light is incident on the electric field enhancing element, and thus LSP in both of the two modes of PPGM and PMGM is generated. Among them, intensity of LSP in PPGM increases as the metallic particles become closer to each other (a distance between the metallic particles becomes smaller). In addition, intensity of LSP in PPGM increases as an amount of a component (a polarization component) of a vibration in an electric field of the excitation light becomes larger in a parallel direction of the metallic particles which are closer to each other. On the other hand, LSP in the mode of PMGM is not greatly influenced by the arrangement of the metallic particles or the polarization direction of the excitation light, and is generated between the metallic particles and the metallic layer (in a lower portion of the metallic particles) due to the irradiation of the excitation light. Then, as described above, PSP is the plasmon which is transmitted through the surface boundary between the metallic layer and the light-transmissive layer, the excitation light is incident on the metallic layer, and thus PSP is isotropically transmitted through the surface boundary between the metallic layer and the light-transmissive layer.

In FIGS. 27A-D, a comparison between one line structure described in the experimental example or the like, and other structures (a basic structure and a hybrid structure) is schematically illustrated. The polarization direction of the excitation light is illustrated by an arrow in the drawings. Furthermore, herein, the expression of the basic structure, the one line structure, and the hybrid structure is a coined word used for discriminating these structures, and hereinafter, the meaning thereof will be described.

First, the basic structure is a structure in which the metallic particles are densely arranged on the light-transmissive layer, and LSPR in PPGM and LSPR in PMGM are excited due to the irradiation of the excitation light. In this example, LSPR in PPGM is generated in both ends of the metallic particles in the polarization direction of the excitation light, but the basic structure has small anisotropy of the arrangement of the metallic particles, and thus even when the excitation light is not polarized light, similarly, LSPR is generated according to a component of an electric field vector of the excitation light. In the basic structure, as a result of densely arranging the metallic particles, it is difficult for the excitation light to reach the metallic layer, and thus PSPR is rarely generated or is not generated at all, and in the drawings, a schematic broken line indicating PSPR is omitted.

Next, the hybrid structure is a structure in which the metallic particles are sparsely arranged on the light-transmissive layer compared to the basic structure, and LSPR in PMGM is excited due to the irradiation of the excitation light. In this example, the metallic particles are separated from each other, and thus LSPR in PPGM is weakly generated compared to the basic structure, but this is not illustrated in the drawings. In the hybrid structure, as a result of sparsely arranging the metallic particles, PSPR (a broken line in the drawings) is generated.

Then, the one line structure is a structure in which the metallic particles are arranged on the light-transmissive layer with intermediate density between the basic structure and the hybrid structure. In the one line structure, there is anisotropy in the arrangement of the metallic particles, and thus LSPR which is generated depends on the polarization direction of the excitation light. Among one line structures, when LSPR⊥PSPR is used (that is, when linearly polarized light is incident in a direction along a direction in which an interval between the metallic particles is narrow), LSPR in PPGM and LSPR in PMGM are excited due to the irradiation of the excitation light. Then, the structure is the one line structure, and thus as a result of sparsely arranging the metallic particles, PSPR (a broken line in the drawings) is generated.

In addition, among the one line structures, when LSPR//PSPR is used (that is, when the linearly polarized light is incident in a direction along a direction in which the interval between the metallic particles is wide), LSPR in PMGM is excited due to the irradiation of the excitation light. In this case, the metallic particles are separated from each other in a direction along the polarization direction of the excitation light, and thus LSPR in PPGM is weak compared to a case of the LSPR⊥PSPR, but this is not illustrated in the drawings. Then, the structure is the one line structure, and thus as a result of sparsely arranging the metallic particles, PSPR (a broken line in the drawings) is generated.

Furthermore, in FIGS. 27A-D, a case where the polarized light is incident is described, but in any structure, when excitation light which is not polarized or circularly polarized light is incident, SPR described above is generated according to a component of a vibration direction in an electric field thereof.

Intensity (an electric field enhancement degree) of entire SPR in each structure correlates with a summation (or a product) of SPR generated in each structure. As described above, a contribution degree of PSPR to the intensity of the entire SPR increases in order of the basic structure<the one line structure<the hybrid structure. In addition, a contribution degree of LSPR (PPGM and PMGM) to the intensity of the entire SPR increases in order of the hybrid structure<the one line structure<the basic structure from a viewpoint of the density (HSD) of the metallic particles. Further, when focusing on LSPR in HSD and PPGM, a contribution degree of LSPR in PPGM to the intensity of the entire SPR increases in order of the hybrid structure<the one line//structure<the one line⊥structure<the basic structure.

As described above, the arrangement of the metallic particles in the electric field enhancing element satisfies a relationship of the following expression (1):

$$P1 < P2 \leq Q + P1 \tag{1}$$

in which P1 represents the first pitch, P2 represents the second pitch, and Q represents a pitch of a diffraction grating satisfying the following expression (2) when an angular frequency of localized plasmon excited to the metallic particle row is ω, a dielectric constant of metal configuring the metallic layer is ∈(ω), a dielectric constant in the vicinity of the metallic particles is ∈, a speed of light in vacuum is c, and an inclined angle from the thickness direction of the metallic layer which is an irradiation angle of the excitation light is θ:

$$(\omega/c) \cdot \{\in \cdot \in(\omega)/(\in + \in(\omega))\}^{1/2} = \in^{1/2} \cdot (\omega/c) \cdot \sin\theta + 2a\pi/Q$$
$$(a = \pm 1, \pm 2, \ldots) \tag{2, and}$$

thus, when classifying according to the structure illustrated in FIGS. 27A-D, the structure belongs to the one line⊥structure or the one line//structure.

The one line⊥structure and the one line//structure are a structure in which LSPR and PSPR with intermediate intensity are mutually interacted (synergistically bonded) to be electromagnetically strong compared to other structures. In addition, in the one line⊥structure, LSPR and PSPR in PPGM with high intensity are mutually interacted to be electromagnetically strong. In addition, in the one line//structure, LSPR and PSPR in PMGM which are generated with the intermediate density (density higher than that of the hybrid structure) are mutually interacted to be electromagnetically strong.

Therefore, in the one line⊥structure and the one line//structure, at least the density of the metallic particles and the contribution ratio of each SPR, and at least a mechanism of enhancing the electric field are different from that of the basic structure in which PSPR is rarely generated, and the hybrid structure in which LSPR in PPGM is rarely generated. Then, in electric field enhancing element having the one line structure, LSPR and PSPR are synergistically and mutually interacted, and thus an extremely high electric field enhancement degree is able to be obtained.

The invention is not limited to the embodiments described above, but is able to be variously changed. For example, the invention includes a configuration which is substantially identical to the configuration described in the embodiment (for example, a configuration including the same function, the same method, and the same result, or a configuration including the same object and the same effect). In addition, the invention includes a configuration in which a portion which is not an essential portion of the configuration described in the embodiment is displaced. In addition, the invention includes a configuration in which a function effect identical to that of the configuration described in the embodiment is obtained or a configuration in which an object identical to that of the configuration described in the embodiment is able to be attained. In addition, the invention includes a configuration in which a known technology is added to the configuration described in the embodiment.

The entire disclosure of Japanese Patent Application No. 2014-027823 filed Feb. 17, 2014 is expressly incorporated by reference herein.

What is claimed is:
1. An analysis apparatus, comprising:
an electric field enhancing element including a metallic layer, a light-transmissive layer which is disposed on the metallic layer and transmits excitation light, and a plurality of metallic particles disposed on the light-transmissive layer, and arranged in a first direction at a first pitch and arranged in a second direction intersecting with the first direction at a second pitch;
a light source configured to irradiate the electric field enhancing element with at least one of linearly polarized light which is polarized in the first direction, linearly polarized light which is polarized in the second direction, and circularly polarized light as the excitation light; and
a detector configured to detect light emitted from the electric field enhancing element,
wherein an arrangement of the metallic particles satisfies a relationship expression (1):

$$P1 < P2 \leq Q + P1 \qquad \text{expression (1):}$$

wherein P1 is the first pitch, P2 is the second pitch, and Q is a pitch of a diffraction grating satisfying expression (2) when an angular frequency of localized plasmon excited to a row of the metallic particles is ω, a dielectric constant of metal configuring the metallic layer is ∈(ω), a dielectric constant in a vicinity of the metallic particles is ∈, a speed of light in vacuum is c, and an inclined angle from a thickness direction of the metallic layer which is an irradiation angle of the excitation light is θ:

$$(\omega/c)\{\cdot\in\cdot\in(\omega)/(\in+\in(\omega))\}^{1/2}=\in^{1/2}\cdot(\omega/c)\cdot\sin\theta+2a\pi/Q$$
$$(a=\pm 1, \pm 2, \ldots), \text{ and} \quad \text{expression (2):}$$

when a thickness of the light-transmissive layer is G nm, an effective refractive index of the light-transmissive layer is $n_{\it eff}$, and a wavelength of the excitation light is $\lambda_i$ nm, a relationship of expression (3) is satisfied:

expression (3):

$$20\text{ nm} < G\cdot(n_{\it eff}/1.46) \le 160\text{ nm}\cdot(\lambda_i/785\text{ nm}) \quad \text{(expression 3).}$$

2. The analysis apparatus according to claim 1, wherein the G, the $n_{\it eff}$, and the $\lambda_i$ satisfy a relationship of expression (4):

$$30\text{ nm} \le G\cdot(n_{\it eff}/1.46) \le 160\text{ nm}\cdot(\lambda_i/785\text{ nm}). \quad \text{expression (4):}$$

3. An electronic device, comprising:
the analysis apparatus according to claim 2;
a calculator configured to calculate medical health information on the basis of detection information from the detector;
storage configured to store the medical health information; and
a display configured to display the medical health information.

4. The analysis apparatus according to claim 1, wherein a ratio of an intensity of localized surface plasmon excited to a corner portion of the metallic particles on a side away from the light-transmissive layer to an intensity of localized surface plasmon excited to a corner portion of the metallic particles on a side close to the light-transmissive layer is constant.

5. An electronic device, comprising:
the analysis apparatus according to claim 4;
a calculator configured to calculate medical health information on the basis of detection information from the detector;
storage configured to store the medical health information; and
a display configured to display the medical health information.

6. An electronic device, comprising:
the analysis apparatus according to claim 1;
a calculator configured to calculate medical health information on the basis of detection information from the detector;
storage configured to store the medical health information; and
a display configured to display the medical health information.

7. An analysis apparatus, comprising:
an electric field enhancing element including a metallic layer, a light-transmissive layer which is disposed on the metallic layer and transmits excitation light, and a plurality of metallic particles disposed on the light-transmissive layer, and arranged in a first direction at a first pitch and arranged in a second direction intersecting with the first direction at a second pitch;
a light source configured to irradiate the electric field enhancing element with at least one of linearly polarized light which is polarized in the first direction, linearly polarized light which is polarized in the second direction, and circularly polarized light as the excitation light; and
a detector configured to detect light emitted from the electric field enhancing element,
wherein an arrangement of the metallic particles satisfies a relationship of expression (1):

$$P1 < P2 \le Q+P1 \quad \text{expression (1):}$$

wherein P1 is the first pitch, P2 is the second pitch, and Q is a pitch of a diffraction grating satisfying expression (2) when an angular frequency of localized plasmon excited to a row of the metallic particles is ω, a dielectric constant of metal configuring the metallic layer is $\in(\omega)$, a dielectric constant in a vicinity of the metallic particles is $\in$, a speed of light in vacuum is c, and an inclined angle from a thickness direction of the metallic layer which is an irradiation angle of the excitation light is θ:

$$(\omega/c)\cdot\{\in\cdot\in(\omega)/(\in+\in(\omega))\}^{1/2}=\in^{1/2}\cdot(\omega/c)\cdot\sin\theta+2a\pi/Q$$
$$(a=\pm 1, \pm 2, \ldots), \quad \text{expression (2):}$$

the light-transmissive layer is formed of a laminated body in which m layers are laminated, m is a natural number, the light-transmissive layer is formed by laminating a first light-transmissive layer, a second light-transmissive layer, a (m−1)-th light-transmissive layer, and a m-th light-transmissive layer in this order from the metallic particle side to the metallic layer side, and when a refractive index in the vicinity of the metallic particles is $n_0$, an angle between a normal direction of the metallic layer and an incident direction of the excitation light is $\theta_0$, an angle between the normal direction of the metallic layer and an incident direction of refracting light of the excitation light in the m-th light-transmissive layer with respect to the metallic layer is $\theta_m$, a refractive index of the m-th light-transmissive layer is $n_m$, a thickness of the m-th light-transmissive layer is $G_m$ nm, and a wavelength of the excitation light is $\lambda_i$ nm, relationships of expression (5) and expression (6) are satisfied:

$$n_0 \cdot \sin\theta_0 = n_m \cdot \sin\theta_m \quad \text{expression (5)}$$

$$20[\text{nm}] < \sum_{m=1}^{m}\{(G_m \cdot \cos\theta_m)\cdot(n_m/1.46)\} \le \quad \text{expression (6)}$$
$$160[\text{nm}]\cdot\lambda_i/785[\text{nm}].$$

8. The analysis apparatus according to claim 7, wherein the $\theta_m$, the $n_m$, the $G_m$, and the $\lambda_i$ satisfy a relationship of expression (7):

$$30[\text{nm}] \le \sum_{m=1}^{m}\{(G_m \cdot \cos\theta_m)\cdot(n_m/1.46)\} \le \quad \text{expression (7)}$$
$$160[\text{nm}]\cdot\lambda_i/785[\text{nm}].$$

9. An electronic device, comprising:
the analysis apparatus according to claim 8;
a calculator configured to calculate medical health information on the basis of detection information from the detector;
storage configured to store the medical health information; and
a display configured to display the medical health information.

10. An electronic device, comprising:
the analysis apparatus according to claim 7;
a calculator configured to calculate medical health information on the basis of detection information from the detector;
storage configured to store the medical health information; and
a display configured to display the medical health information.

* * * * *